United States Patent
Volland et al.

(10) Patent No.: US 7,615,645 B2
(45) Date of Patent: Nov. 10, 2009

(54) METHOD FOR THE CONTINUOUS PRODUCTION OF ALDEHYDES

(75) Inventors: Martin Volland, Heidelberg (DE); Thomas Mackewitz, Römerberg (DE); Wolfgang Ahlers, Worms (DE); Ansgar Schäfer, Karlsruhe (DE); Wolfgang Richter, Wachenheim (DE); Rocco Paciello, Bad Dürkheim (DE)

(73) Assignee: BASF Aktiengesellschaft (DE)

( * ) Notice: Subject to any disclaimer, the term of this patent is extended or adjusted under 35 U.S.C. 154(b) by 520 days.

(21) Appl. No.: 10/575,843

(22) PCT Filed: Oct. 14, 2004

(86) PCT No.: PCT/EP2004/011530

§ 371 (c)(1),
(2), (4) Date: Apr. 13, 2006

(87) PCT Pub. No.: WO2005/042458

PCT Pub. Date: May 12, 2005

(65) Prior Publication Data

US 2007/0004939 A1   Jan. 4, 2007

(30) Foreign Application Priority Data

Oct. 21, 2003   (DE) .................. 103 49 482
Aug. 24, 2004   (DE) .................. 10 2004 041 144

(51) Int. Cl.
*C07C 45/50* (2006.01)
*C07D 207/00* (2006.01)

(52) U.S. Cl. ............... 548/400; 568/8; 568/451; 568/453

(58) Field of Classification Search ............ 548/400; 568/8, 451, 453
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,599,206 A | 7/1986 | Billig et al. |
| 4,668,651 A | 5/1987 | Billig et al. |
| 4,716,250 A | 12/1987 | Abatjoglou et al. |
| 4,769,498 A | 9/1988 | Billig et al. |
| 4,778,929 A | 10/1988 | Zehner et al. |
| 4,885,401 A | 12/1989 | Billig et al. |
| 5,728,893 A | 3/1998 | Becker et al. |
| 5,744,650 A | 4/1998 | Nicholson et al. |
| 5,808,168 A | 9/1998 | Bahrmann et al. |
| 5,849,972 A | 12/1998 | Vicari et al. |
| 5,874,639 A | 2/1999 | Nicholson et al. |
| 6,100,432 A | 8/2000 | Borgel et al. |
| 6,342,605 B1 | 1/2002 | Geissler et al. |
| 6,538,168 B1 | 3/2003 | Schwab et al. |
| 6,580,009 B2 | 6/2003 | Schwab et al. |
| 6,642,420 B1 | 11/2003 | Zehner et al. |
| 6,727,391 B2 | 4/2004 | Walczuch et al. |
| 6,737,555 B1 | 5/2004 | Maas et al. |
| 6,977,312 B2 | 12/2005 | Ahlers et al. |
| 7,015,361 B2 | 3/2006 | Zehner et al. |
| 2004/0110960 A1 | 6/2004 | Ahlers et al. |

FOREIGN PATENT DOCUMENTS

| | | |
|---|---|---|
| EP | 0 188 426 | 4/1985 |
| EP | 0 155 508 | 9/1985 |
| EP | 0 213 369 | 3/1987 |
| EP | 0 423 769 | 4/1991 |
| EP | 0 982 314 | 3/2000 |
| EP | 1 008 580 | 6/2000 |
| EP | 1 069 101 | 1/2001 |
| EP | 1 114 017 | 7/2001 |
| EP | 1 134 271 | 9/2001 |
| EP | 1 231 198 | 8/2002 |
| JP | 2000-143572 | 5/2000 |
| WO | WO-85/01567 | 4/1985 |
| WO | WO-97/20801 | 6/1987 |
| WO | WO-98/19985 | 5/1998 |

(Continued)

OTHER PUBLICATIONS d'Oro, Paolo Cavalier et al., "Propene Hydroformylation with Rhodium Carbonyls and Triphenylphosphine", La Chimica et L'Industria 62 (1980), pp. 572-579.

(Continued)

*Primary Examiner*—Golam M. M. Shameem
*Assistant Examiner*—Susannah Chung
(74) *Attorney, Agent, or Firm*—Connolly Bove Lodge & Hutz LLP

(57) ABSTRACT

The invention relates to a method for the continuous production of aldehydes by the isomerising hydroformylation in a homogenous phase of olefin compositions by means of a synthesis gas, in the presence of a homogeneous rhodium catalyst that is complexed with an organophosphorus ligand containing oxygen atoms and/or nitrogen atoms and a free ligand. The production is carried out at high temperature and high pressure in a multi-stage reaction system consisting of at least two reaction zones. According to the method, the olefin composition is first reacted in a first reaction zone or a group of several first reaction zones at a total pressure of between 10 and 40 bar, using a synthesis gas with a $CO/H_2$ molar ratio of between 4:1 and 1:2 until a 40 to 95% conversion of the α-olefins is obtained.

12 Claims, 1 Drawing Sheet

FOREIGN PATENT DOCUMENTS

| | | |
|---|---|---|
| WO | WO-98/52632 | 11/1998 |
| WO | WO-99/50214 | 10/1999 |
| WO | WO-99/52632 | 10/1999 |
| WO | WO-00/53546 | 9/2000 |
| WO | WO-01/58589 | 8/2001 |
| WO | WO-01/58844 | 8/2001 |
| WO | WO-02/068371 | 9/2002 |
| WO | WO02/068371 * | 9/2002 |
| WO | WO-02/083695 | 10/2002 |

OTHER PUBLICATIONS

Yang, Chao et al., "Kinetics of Hydroformylation of Propylene Using RhCl(CO)(TPPTS)2/TPPTS Complex Catalyst in Aqueous System", Catalysis Today 74 (2002), pp. 111-119.

Reinius, H. K. et al., "The Effects of Process Variables in the Hydroformylation of Methyl Methacrylate with the In Situ Formed (*o*-thiomethylphenyl) diphenylphosphine Rhodium Complex", Journal of Molecular Catalysis A: Chemical 158 (2000), pp. 499-508.

Weissermel, Klaus et al., Industrielle Organische Chemie, 5th Ed., Wiley-VCH, 1998, pp. 82-89.

* cited by examiner

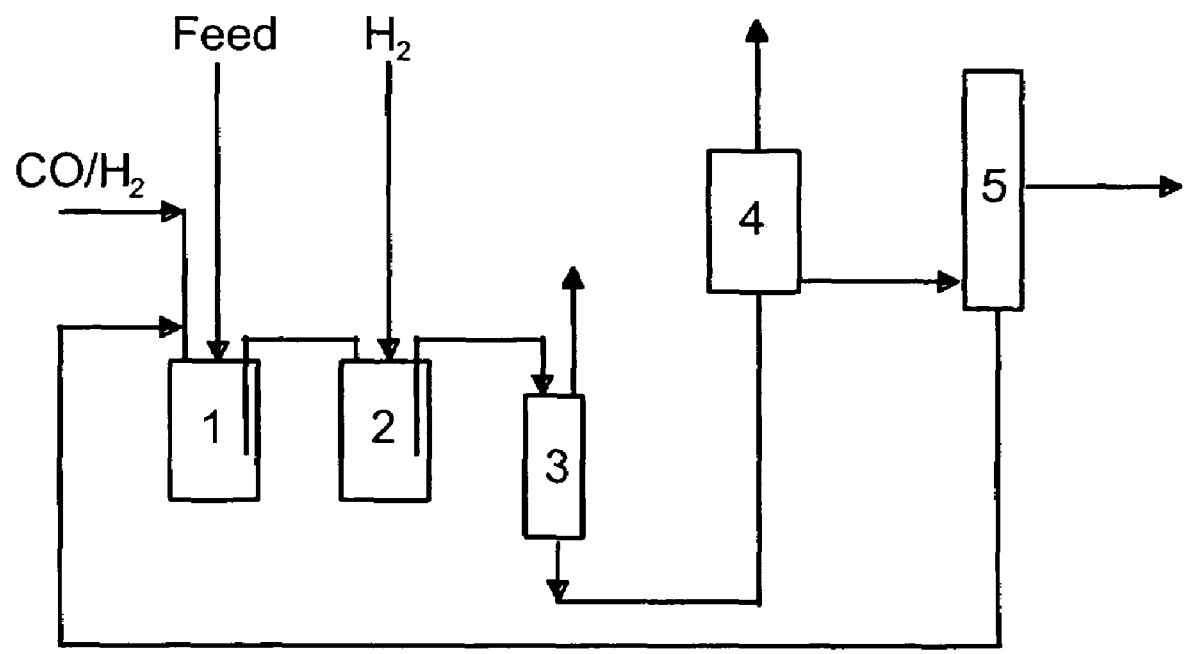

METHOD FOR THE CONTINUOUS PRODUCTION OF ALDEHYDES

RELATED APPLICATIONS

This application is a national stage application (under 35 U.S.C. 371) of PCT/EP2004/011530 filed Oct. 14, 2004 which claims benefit to German application 103 49 482.0 filed Oct. 21, 2003 and German application 10 2004 041 144.1 filed Aug. 24, 2004.

The present invention relates to a process for the continuous preparation of aldehydes having from 5 to 21 carbon atoms by isomerizing hydroformylation in the homogeneous phase of olefin compositions having from 4 to 20 carbon atoms and comprising α-olefins and olefins having internal double bonds by means of synthesis gas in the presence of a homogeneous rhodium catalyst complexed with an oxygen- and/or nitrogen-containing organophosphorus ligand and free ligand at elevated temperature and elevated pressure in a multistage reaction system comprising at least two reaction zones.

In 1990, the annual world production of products from the hydroformylation of olefins, also known as the oxo process, was estimated to be about 7 million metric tons. Although mostly homogeneous catalysts based on cobalt were employed at the beginning of the industrial application of the oxo process, homogeneous hydroformylation catalysts based on rhodium have been increasingly used in industry since the 1970s because they make it possible to work economically at lower temperatures and, in particular, at a lower pressure than in the case of cobalt catalysts and achieve a high n/i selectivity in the hydroformylation of olefins having a terminal double bond (α-olefins). For this reason, the low-pressure hydroformylation using generally triphenylphosphine-modified rhodium complexes has virtually completely displaced the high-pressure hydroformylation using cobalt carbonyl catalysts in the industrial preparation of $C_3$- and $C_4$-aldehydes from ethene and propene, respectively. Nevertheless, the high-pressure hydroformylation using cobalt carbonyl catalysts is still of considerable industrial importance even today, in particular in the hydroformylation of long-chain olefins having internal double bonds. Such olefins are available in large quantities, for example as raffinate II (from the C4 cut of a steam cracker after removal or selective hydrogenation of dienes, such as 1,3-butadiene and removal of isobutene-based $C_4$ mixture comprising butene-1 and butene-2) or from olefin dimerization processes and trimerization processes or from olefin metathesis plants and Fischer-Tropsch plants and their oxo products serve as starting materials for the preparation of other industrial products such as plasticizers or surfactant alcohols. Owing to the way in which they are produced, these olefins are generally in the form of an isomer mixture of α-olefin concerned and the corresponding structural isomers having an internal double bond and are used in this form as starting material for the oxo process. For the purposes of the present invention "internal" olefins are accordingly olefins whose double bond is, unlike α-olefins, not terminal but located in the interior of the olefin molecule.

The reason why cobalt catalysts are preferred for the hydroformylation of such relatively long-chain olefin mixtures and also for the hydroformylation of individual olefinic compounds having internal double bonds despite the higher temperatures and higher pressures required when using cobalt catalysts may be found in the different catalytic behavior of the catalyst metals cobalt and rhodium. In the hydroformylation of α-olefins, it is possible, depending on the site of addition of the CO molecule to the double bond in accordance with the equation (1)

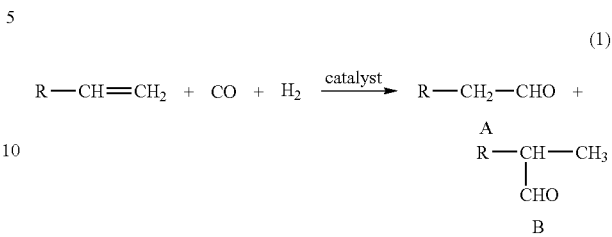

for linear aldehydes A, known as n-aldehydes, or branched aldehydes B, also referred to as iso-aldehydes, to be formed. In general, a higher proportion of n-aldehydes in the hydroformylation product, expressed by the n/i ratio, i.e. the molar ratio of n-aldehydes to iso-aldehydes in the reaction product, is desired. Although the rhodium-triphenylphosphine catalyst system leads to high n selectivities in the hydroformylation of short-chain α-olefins, this catalyst system has disadvantages in the hydroformylation of the abovementioned olefin mixtures or olefins having internal double bonds. Firstly, the rhodium-triphenylphosphine catalyst system displays only a very low hydroformylation activity toward internal double bonds, with the result that such "internal" olefins either do not react at all or react to an ecomically acceptable extent only when using uneconomically long reaction times, and, secondly, this disadvantage is made worse by the fact that this catalyst system also isomerizes terminal double bonds to internal double bonds to a significant extent under the conditions of the hydroformylation reaction, so that when the rhodium-triphenylphosphine catalyst system is used in the hydroformylation of such industrial olefin isomer mixtures or internal olefins, only unsatisfactory olefin conversions and unsatisfactory degrees of utilization of the internal olefins are achieved.

To be able to utilize the inherent advantages of the low-pressure hydroformylation using rhodium catalysts in the hydroformylation of relatively long-chain olefin mixtures of α-olefins and internal olefins and the hydroformylation of internal olefins, efforts have long been made to develop rhodium-catalyzed "isomerizing" hydroformylation processes, viz. processes in which the proportion of n-aldehydes in the reaction product from the hydroformylation of internal olefins or mixtures of α-olefins and internal olefins is higher than would have been expected from the proportions of terminal and internal double bonds in the starting olefin and the double bond isomerization effected by the rhodium-triphenylphosphine catalyst system. Research aimed at achieving this goal has hitherto focused on modification of the properties of the rhodium catalyst by means of suitable ligands and/or process engineering measures. However, there is still a need for considerable improvement in order to achieve economically successful use in isomerizing hydroformylation in industrial practice.

As rhodium catalyst systems suitable for isomerizing hydroformylation, mention may be made by way of example of merely the rhodium complexes with organophosphite ligands described in U.S. Pat. No. 3,527,809, the rhodium complexes with chelating organophosphite ligands described in U.S. Pat. No. 4,668,651 and the rhodium complexes with organophosphoramidite ligands and organophosphite or organophosphonite ligands described in WO 01/58589 and WO 02/83695.

Since the n/i selectivity in the hydroformylation of olefins is influenced by many parameters, the use of such catalysts for isomerizing hydroformylation has to be accompanied by process engineering measures and measures involving the reaction conditions in order to achieve economically satisfactory results. One parameter which has already been identified by d' Oro et al, LA CHIMICA ET L'INDUSTRIA 62, 572 (1980) as having a significant influence on the n/i selectivity in hydroformylations using the rhodium-triphenylphosphine catalyst system is the CO partial pressure in the hydroformylation reactor. It was in this case found that although reducing the CO partial pressure leads to an increase in the n selectivity, such a reduction in the CO partial pressure results in an undesirably large increase in the hydrogenation rate of the olefins used, and thus a high level of paraffin formation.

In U.S. Pat. No. 4,885,401, it is stated that a reduction in the CO partial pressure in the hydroformylation reactor when using rhodium-chelating phosphite catalyst systems leads to an increase in the reaction rate and that the CO/$H_2$ ratio should preferably be from 1:1 to 1:10.

Example 12 of U.S. Pat. No. 4,885,401, which concerns the hydroformylation of 2-butene, indicates that although the reaction rate is increased when the CO/$H_2$ ratio is reduced, the n/i ratio of the aldehydes formed decreases.

U.S. Pat. No. 4,885,401 mentions in general terms the possibility of hydroformylating mixtures of α-olefins and internal olefins in a series of different reactors and, if desired, setting the optimum reaction conditions independently in the individual reactors, but specific teachings on the way in which this should be done and the direction of the optimization measures are not provided.

U.S. Pat. No. 4,599,206 contains examples relating to the hydroformylation of butene-1/butene-2 mixtures using a rhodium organomonophosphite ligand catalyst in two successive reactors which are operated at different CO/$H_2$ molar ratios. However, the greatly varying reaction conditions of these examples make it impossible to discern from the individual results any generalizable teaching as to how to conduct an isomerizing hydroformylation to achieve high n/i ratios of the product aldehydes coupled with a high butene conversion.

EP-A 188 426 describes a process for the hydroformylation of olefins in which the olefin-containing offgas from a first reactor system is fed into a second reactor system which is decoupled from the first reactor system to complete the hydroformylation. It is possible for the reaction conditions employed in the second decoupled reactor system to be different from those employed in the first, in particular different catalyst systems can be employed there. The use of these decoupled reactor systems is said to achieve more efficient and more complete utilization of the olefins fed in. EP-A 188 426 does not refer to hydroformylation under isomerizing conditions and the examples in this document are accordingly restricted to the use of the rhodium-triphenylphosphine catalyst system for the hydroformylation of propene. Furthermore, there are no teachings as to how the n/i ratio can be increased when using internal olefins as starting material.

WO 97/20801 ($\hat{=}$ U.S. Pat. No. 5,744,650) specifically addresses the relationship between hydroformylation rate and carbon monoxide partial pressure in hydroformylations using rhodium-organopolyphosphite catalysts, the prevention of or reduction in the deactivation of the rhodium-organopolyphosphite catalyst, the prevention of and/or reduction in periodic fluctuations in the carbon monoxide partial pressure, the hydrogen partial pressure, the total reaction pressure, the hydroformylation rate and/or the temperature during the hydroformylation process and proposes, as a solution to these problems, that the hydroformylation process be carried out at a carbon monoxide partial pressure which is such that the hydroformylation rate increases when the carbon monoxide partial pressure decreases and the hydroformylation rate decreases when the carbon monoxide partial pressure increases and that one or more of the following conditions are met:

a) the use of a temperature which is such that the temperature difference between the temperature of the reaction product liquid and the inlet temperature of the coolant is less than 25° C., b) a carbon monoxide conversion of less than 90%, c) a hydrogen conversion of more than 65% and d) a conversion of the olefinically unsaturated compound of more than 50%.

As regards the effects of the carbon monoxide partial pressure on the n/i selectivity, WO 97/20801 merely observes that working in a range in which the hydroformylation has a negative order of reaction in respect of the carbon monoxide partial pressure, i.e. at a relatively high carbon monoxide partial pressure, leads to a high isomer ratio.

The continuation-in-part patent U.S. Pat. No. 5,874,639 extends the subject-matter of U.S. Pat. No. 5,744,650 to the use of catalysts comprising organopolyphosphorus-metal complexes.

U.S. Pat. No. 5,728,893 relates to the use of a specifically constructed multistage reactor for hydroformylations, with the purpose of achieving reaction conditions in which a change in the n product selectivity of 0.2% of n product per 1 pound per square inch of CO partial pressure ($\hat{=}$ 2.9% per bar of CO partial pressure) is not exceeded. The only examples in this patent concern the conventional hydroformylation of ethylene and propene using the rhodium-triphenylphosphine catalyst system and using an excess of hydrogen from the beginning. According to the data from the examples, an increase in the CO partial pressure leads to a reduction in the hydroformylation rate. No information is given about the n/i ratio of the butyraldehydes produced in the hydroformylation of propene in Example 2.

According to JP-A 143 572 (2000), the hydroformylation should be carried out under conditions under which the carbon monoxide partial pressure in the reactor has virtually no effect on the reaction rate.

Reinius et al (J. Mol. Cat. A: Chemical 158, 499 (2000)) studied the hydroformylation of methyl methacrylate using a rhodium-methyl(thienyl)diphenylphosphine complex as catalyst and came to the conclusion that increasing the $H_2$ partial pressure in the synthesis gas does not alter the n/i selectivity of the hydroformylation reaction, in contrast to the situation when a triphenylphosphine-rodium complex is used as catalyst.

In Catalysis Today 74, 111 (2002), Yang et al. describe the influence of the $H_2$ and CO partial pressure on the catalytic activity of the rhodium-tris(sodium m-sulfonatophenyl)phosphine complex in the hydroformylation of propene. They found that in the case of this catalyst system the hydroformylation rate increases with increasing $H_2$ partial pressure and decreases with increasing CO partial pressure.

EP-A 423 769 relates to the use of a combination of two different reactors connected to form a reactor cascade in the multistage hydroformylation of olefins. According to the examples in this patent application, the hydroformylation of propene in the presence of the conventional rhodium-triphenylphosphine catalyst system is carried out using synthesis gas mixtures in which the proportion of hydrogen exceeds the proportion of carbon monoxide both in the first and second reaction stages. EP-B 423 769 gives no information on isomerizing hydroformylation.

EP-A 1 008 580 likewise relates to the use of a reactor cascade comprising at least two reactors which are divided into pressure sections for hydroformylation, where the relationship between the $H_2$ and CO partial pressures in the first (m−1)-th pressure section and the corresponding partial pressures in a downstream second (m-th) pressure section is in accordance with at least one of the following inequalities, $$p_{CO}(m-1) < p_{CO}(m)$$

$$p_{H2}(m-1) < p_{H2}(m)$$

$$p_{CO}(m-1) + p_{H2}(m-1) < p_{CO}(m) + p_{H2}(m)$$

where $p_{CO}$ and $p_{H2}$ are the CO and $H_2$ partial pressures in the respective pressure section or reaction stage. This mode of operation is said to increase the hydroformylation rate and also improve the n/i selectivity. According to the examples in EP-A 1 008 580, this is achieved in the hydroformylation of an octene mixture using synthesis gas having a $CO/H_2$ molar ratio of 1:1 by setting a pressure of 50 kg/cm$^2$ in the first reaction stage and a pressure of 170 kg/cm$^2$ in the second reaction stage. The hydroformylation catalyst used here is uncomplexed hydridorhodium carbonyl which is generated in situ in the reactor. Although it is said in the description of EP-A 1 008 580 that this process is also suitable for hydroformylations using cobalt and rhodium catalysts complexed with various phosphite or phosphine ligands, specific examples and information on the effects of this process on the n/i ratio of the aldehydes produced when using catalysts which behave differently from uncomplexed rhodium are lacking.

Carrying out a second reaction stage at a CO partial pressure which is higher than the CO partial pressure in the first reaction stage is also disclosed by U.S. Pat. No. 4,716,250 (Example 9) for the hydroformylation of 1-octene by means of a rhodium catalyst complexed with a monosulfonated phosphine. As regards the $CO/H_2$ ratio in the individual reaction stages, an excess of hydrogen is present in both the first and second reaction stages. However, the best result in respect of the n/i ratio of the nonanals formed (n/i ratio=12.3) is achieved in a variant different from Example 9 when using an approximately equal CO partial pressure in the first and second stages and when using a high $H_2/CO$ molar ratio both in the first and second reaction stages.

WO 02/68371 relates to an isomerizing hydroformylation process in a reactor cascade using a conventional rhodium-triphenylphosphine catalyst in the first reaction stage and a rhodium catalyst modified with a chelating diphosphine having a xanthene backbone in the second reaction stage. When a synthesis gas having a $CO/H_2$ ratio of 1:1 is used, the second reaction stage in this document is, according to the examples, also carried out at a pressure higher than that in the first stage, corresponding to an increase of the CO and $H_2$ partial pressures over the partial pressures in the first stage. However, the use of different catalyst systems is complicated, which considerably increases the costs of this process.

It is an object of the present invention to find a process for the hydroformylation of mixtures of internal olefins and α-olefins which, despite the opposite dependences of the reaction rate and the n selectivity on the CO partial pressure as indicated by the prior art, makes it possible to prepared aldehydes economically from such olefin mixtures with a high n selectivity and at a high space-time yield. For this purpose the isomerization of internal double bonds to terminal double bonds in the internal olefins present in the olefin mixture should be promoted and at the same time the double bond izomerization of α-olefins to internal olefins should be suppressed, since the latter reduces the total space-time yield of the process because internal olefins are basically less reactive than α-olefins.

We have found that this object is achieved by a process for the continuous preparation of aldehydes having from 5 to 21 carbon atoms by isomerizing hydroformylation in the homogeneous phase of olefin compositions having from 4 to 20 carbon atoms and comprising α-olefins and olefins having internal double bonds by means of synthesis gas in the presence of a homogeneous rhodium catalyst complexed with an oxygen- and/or nitrogen-containing organophosphorus ligand and free ligand at elevated temperature and elevated pressure in a multistage reaction system comprising at least two reaction zones, wherein the olefin composition is firstly reacted with synthesis gas having a $CO/H_2$ molar ratio of from 4:1 to 1:2 at a total pressure of from 10 to 40 bar in a group of one or more first reaction zones to a conversion of the α-olefins of from 40 to 95% and the hydroformylation mixture from this group of one or more first reaction zones is reacted with synthesis gas having a $CO/H_2$ molar ratio of from 1:4 to 1:1000 at a total pressure of from 5 to 30 bar in a group of one or more downstream reaction zones, where the total pressure in the one or more downstream reaction zones is in each case at least from 1 to (T1−Tf) bar lower than in the preceding reaction zone, where T1 is the total pressure in the preceding reaction zone and Tf is the total pressure in the reaction zone downstream of the one or more first reaction zones, with the proviso that the difference T1−Tf is greater than 1 bar, and the CO partial pressure in the one or more downstream reaction zones is in each case lower than in the preceding reaction zone.

The process of the present invention is based on a number of research results concerning isomerizing hydroformylation. Thus, it has been found, inter alia, that a) in the continuous hydroformylation of raffinate II in two reactors connected in series under otherwise identical conditions in both reactors, a decrease in the CO partial pressure, achieved either by reducing the synthesis gas pressure at a constant $CO/H_2$ molar ratio or by reducing the $CO/H_2$ molar ratio at a constant total pressure, results in an increase in the aldehyde yield and the proportion of n-valeraldehyde in the hydroformylation product mixture;

b) in the batchwise hydroformylation of 2-butene, a reduction in the CO partial pressure leads to an increase in the aldehyde yield and the proportion of n-valeraldehyde; and c) in the batchwise hydroformylation of 1-butene, a reduction in the CO partial pressure leads to an increase in the undesirable isomerization of 1-butene to 2-butene and both the space-time yield of aldehyde formation and the n/i ratio of the valeraldehydes formed decrease as a consequence.

As a result of use of the measures according to the present invention and setting the process parameters according to the present invention, the α-olefin present in the olefin composition is, according to the present invention, mostly converted, i.e. to a conversion of from 40 to 95%, preferably from 70 to 95%, to the corresponding n-aldehyde in a group of one or more first reaction zones, without isomerization of the terminal double bond to internal double bonds occurring to a substantial extent, so that, in greatly simplified terms, the olefins having internal double bonds in the olefin composition are hydroformylated in a group of one or more downstream reaction zones under hydroformylation conditions which are optimal for the isomerization of internal double bonds to terminal double bonds without this leading to significant isomerization of the α-olefin originally present in the olefin composition, so that an aldehyde product having a high n/i ratio is finally obtained in a high space-time yield from the olefin composition. The extent of undesirable isomerization of the α-olefins to internal olefins in the group of one or more first reaction zones under the hydroformylation conditions should be kept as small as possible and be not more than 80%, preferably less than 50% and particularly preferably less than 30%.

The sought-after conversion of generally from 50 to 99% of the α-olefins present in the olefin composition can thus be brought about in a single first reaction zone or in a plurality of first reaction zones. For the purposes of the present invention, the expression "group of one or more first reaction zones" will be used to refer to this single first reaction zone or a plurality of first reaction zones. The same applies to the single reaction zone or plurality of reaction zones downstream of the group of one or more first reaction zones. In this "group of one or more downstream reaction zones", the main objective is the isomerizing hydroformylation of the internal olefins in the olefin composition to be hydroformylated.

The process of the present invention thus differs from the prior art relating to the stepwise hydroformylation of olefin mixtures comprising α-olefins and internal olefins by means of reaction zones which are cascaded, i.e. gradated, in respect of the pressure and the $CO/H_2$ ratio (e.g. U.S. Pat. No. 4,716,250; EP-A 1 008 580), in that both the CO partial pressure and the total pressure are lower in the group of one or more downstream reaction zones than in the group of one or more first reaction zones, with the group of one or more first reaction zones generally being operated at a relatively high $CO/H_2$ molar ratio and a significantly higher total pressure than the group of one or more downstream reaction zones.

In the process of the present invention, the hydroformylation of olefin compositions having terminal and internal double bonds is carried out in a multistage reaction system which is cascaded in respect of the process parameters total pressure, $CO/H_2$ molar ratio and CO partial pressure and comprises a plurality of reaction zones, e.g. from 2 to 10, preferably from 2 to 4 and particularly preferably two (2) reaction zones, connected in series, where the individual reaction zones differ from one another in terms of the different total pressure, the CO partial pressure and, if desired, the $CO/H_2$ molar ratio prevailing therein. Thus, the individual reaction zones can be present in the individual reactors connected in series in a reactor cascade, or a single reaction zone can also encompass a plurality of reactors which are connected in series or in parallel and which meet the criteria according to the present invention for an individual reaction zone, essentially the same total pressure and CO partial pressure. Conversely, a single hydroformylation reactor can be segmented by means of suitable internals into a plurality of reaction compartments in which the reaction conditions can be set independently so that one or more of these reaction compartments form a reaction zone and one or more of the downstream reaction compartments of the reactor form, depending on the setting of the process parameters in the individual compartments, a second reaction zone or a plurality of downstream reaction zones. Thus, if a downstream compartment of the reactor is operated at a total pressure which is at least 1 bar lower and the CO partial pressure is lower, if desired at a lower $CO/H_2$ molar ratio, than in the preceding compartment, this downstream compartment forms a new reaction zone compared to the preceding compartment. Analogous considerations apply to the reaction conditions in individual reactors connected in series.

As reactors for the process of the present invention, it is in principle possible to use all types of reactors which are suitable for hydroformylation reactions, for example stirred reactors, bubble column reactors as described, for example, in U.S. Pat. No. 4,778,929, circulation reactors as described, for example, in EP-A 1 114 017, tube reactors, in the case of which the individual reactors of a series can have different mixing characteristics, as described, for example, in EP-A 423 769, and also compartmentalized reactors as described, for example, in EP-A 1 231 198 or in U.S. Pat. No. 5,728,893.

If a reaction zone encompasses a plurality of reactors, it is possible to use identical or different reactor types in this reaction zone, and it is likewise possible to use identical or different reactor types from reaction zone to reaction zone. Preference is given to using the same reactor types in the individual reaction zones, e.g. circulation reactors or stirred vessels.

The process of the present invention is generally carried out at a total pressure of generally from 10 to 40 bar, preferably from 10 to 30 bar and particularly preferably from 10 to 25 bar, in the group of one or more first reaction zones and at a total pressure of generally from 5 to 30 bar, preferably from 5 to 20 bar and particularly preferably from 9 to 20 bar, in the group of one or more reaction zones downstream of the group of one or more first reaction zones. The total pressure in the individual reaction zones is the sum of the partial pressures of the reaction gases carbon monoxide (CO) and hydrogen ($H_2$), the partial pressures of the individual olefins in the olefin composition to be hydroformylated and the aldehydes produced during the hydroformylation and the partial pressures of further components present in the reaction mixture, e.g. saturated hydrocarbons, inert gases such as nitrogen, auxiliaries such as solvents or free ligand, any stabilizers, e.g. tertiary amines or azines, added to the reaction mixture to stabilize the ligands used against degradation reactions and any impurities present in traces in the starting materials, e.g. carbon dioxide, and by-products formed during the hydroformylation. In general, the total pressure in the individual reaction zones is set via the introduction of the reaction gases CO and $H_2$ and/or via the removal of volatile components by depressurization of the reaction mixture at the respective reaction temperature.

According to the present invention, the total pressure in the individual reaction zones is set so that the total pressure in a downstream reaction zone is at least from 1 to (T1−Tf) bar lower than in the preceding reaction zone, where T1 is the total pressure in the preceding reaction zone $R_m$ which can in turn be preceded by one or more reaction zones, e.g. $R_i$, $R_k$, etc., and Tf is the total pressure in the reaction zone $R_n$ downstream of this reaction zone, where the reaction zone $R_n$ can in turn be followed by further reaction zones ($R_o$, $R_p$, etc.) in which the total pressure obeys the same relationship as that between the reaction zones $R_m$ and $R_n$. Here, the proviso that the difference T1−Tf is greater than 1 bar applies. In general, the total pressure in the downstream reaction zone $R_n$ is from 1 to 25 bar lower, preferably from 1 to 15 bar lower and particularly preferably from 1 to 10 bar lower, than in the preceding reaction zone. The reference point for the total pressure in the individual reaction zones is in each case the total pressure in the reactor—or if a plurality of reactors together form a reaction zone, the total pressure in the last reactor of the preceding reaction zone and in the reactor—or if a plurality of reactors together form a reaction zone; the total pressure in the first reactor of the downstream reaction zone. Corresponding considerations apply to compartmentalized reactors in which one or more individual reaction compartments form a reaction zone. In the case of tube reactors, the total pressure at the outlet of a first tube reactor and the total pressure at the inlet into a downstream tube reactor or other reactors forms the reference point for determining the individual reaction zones. If the total pressure difference between two or more reactors or reaction compartments connected in series is less than 1 bar, these together form a reaction zone.

The reaction temperature in the individual reaction zones is generally from 50 to 200° C., preferably from 50 to 150° C. and particularly preferably to 70 to 130° C.

The $CO/H_2$ molar ratio of the synthesis gas in the group of one or more first reaction zones in the process of the present invention is generally from 4:1 to 1:2, preferably from 4:1 to 2:3 and particularly preferably from 3:2 to 2:3 ($CO:H_2$), and that in the group of one or more reaction zones downstream of the group of one or more first reaction zones is generally from 1:4 to 1:1000, preferably from 1:4 to 1:100 and particularly preferably from 1:9 to 1:100 ($CO/H_2$), where the CO partial pressure in a downstream reaction zone is set to a value lower than the CO partial pressure prevailing in the reaction zone immediately preceding this reaction zone. In general, the CO partial pressure in the reaction zone downstream of the one or more first reaction zones is set to a value which is from 1 to 20 bar lower, preferably from 1 to 10 bar lower and particularly preferably from 2 to 7 bar lower, than the CO partial pressure prevailing in the immediately preceding reaction zone.

As regards the reference points for determining the CO partial pressure in the individual reaction zones, what has been said above for determining the total pressure in the individual reaction zones applies analogously.

The optimum total pressure, the optimum $CO/H_2$ molar ratio and also the optimum CO partial pressure in the individual reaction zones of the process of the present invention depends on the type and composition of the olefin composition to be hydroformylated, for example the chain length of the olefins to be hydroformylated, the proportions of terminal and internal double bonds, the position of the internal double bonds and possibly the degree of branching of the olefins. Accordingly, these process parameters are, according to the present invention, advantageously optimized for a particular olefin composition and the hydroformylation catalyst being used in routine preliminary experiments or mathematical process simulations in order to find the conditions which are economically optimal for achieving a very high n/i ratio in the aldehyde product at a very high space-time yield.

Similar considerations apply to the number of reaction zones in the process of the present invention. Thus, it can be useful, for the purposes of the present invention, to arrange up to 10 reaction zones in series to achieve an economically optimal combination of n/i ratio and space-time yield. Owing to the resulting higher capital costs and/or cost of instrumentation and possibly higher operating costs, this can neutralize the economic advantage gained by the improvement in the n/i ratio and the space-time yield. For this reason, the process of the present invention is advantageously carried out in generally from 2 to 8, preferably from 2 to 4 and particularly preferably 2, reaction zones connected in series, with the economically optimal number of reaction zones advantageously being determined in the individual case as a function of the type and composition of the olefin composition to be hydroformylated and the hydroformylation catalyst used by means of routine experiments or mathematical process simulations.

It is possible for the hydroformylation product mixture from one reaction zone to be depressurized before entry into the subsequent reaction zone, the aldehydes formed to be separated off and the unreacted olefins be fed into the next reaction zone to be hydroformylated. According to the present invention, preference is given to carrying out no such work-up of the hydroformylation product mixture from one reaction zone before it enters the next reaction zone and depressurizing the hydroformylation product mixture from one reaction zone directly into the next reaction zone. This advantageous embodiment of the process of the present invention is made possible by the total pressure in the downstream reaction zone being lower than in the preceding reaction zone.

The total pressure in the individual reaction zones is generally set as a function of the amount of freshly introduced synthesis gas by regulating the offgas stream from the individual reaction zones, which is generally composed essentially of unreacted synthesis gas, inert gases and hydrocarbons. To set the desired $CO/H_2$ molar ratio in the individual reaction zones if the $CO/H_2$ mixture is not introduced with the desired, preset $CO/H_2$ molar ratio into the individual reaction zones, it can be advantageous to use synthesis gas having a conventional $CO/H_2$ molar ratio of about 1:1 and to set the desired $CO/H_2$ molar ratio in the individual reaction zones by metering in additional amounts of CO or $H_2$. Here, there is an economically advantageous opportunity of integrating the process of the present invention with other processes by using essentially CO- or $H_2$-containing offgases from other processes to adjust the $CO/H_2$ molar ratio. Thus, for example, the CO-containing offgas from methyl formate production can be used to increase the $CO/H_2$ molar ratio or the $H_2$-containing offgas from the hydrogenation of aldehydes or enals produced therefrom, e.g. 2-ethylhexenal or 2-propylheptenal, to the corresponding saturated alcohols can be used as $H_2$ source for reducing the $CO/H_2$ molar ratio in individual reaction zones. The CO partial pressure can also be reduced by lowering the $CO/H_2$ pressure in a downstream reaction zone.

The process of the present invention is suitable for the hydroformylation of olefin compositions comprising preferably aliphatic $C_4$-$C_{20}$-olefins which have internal and terminal double bonds and may be linear or branched. Examples of such olefin compositions are 1-butene/2-butene mixtures as are obtained industrially as, for example, raffinate II. The term raffinate II refers to the $C_4$-olefin fraction obtained after butadienes and acetylenes and subsequently isobutene have been separated off from the $C_4$ fraction from steam crackers. This generally has the following composition:

from 0.5 to 5% by weight of isobutane,
from 5 to 20% by weight of n-butane,
from 20 to 40% by weight of trans-2-butene,
from 10 to 20% by weight of cis-2-butene,
from 25 to 55% by weight of 1-butene,
from 0.5 to 5% by weight of isobutene and also trace gases such as 1,3-butadiene, propadiene, propene, cyclopropane, methylcyclopropane and vinylacetylene.

Other suitable olefin compositions are, for example, pentene mixtures as are formed, for example, in the acid-catalyzed codimerization of ethene and propene, hexene mixtures from the acid- or nickel-catalyzed (Dimersol process) dimerization of propene or from metathesis processes as described, for example, in EP-A 1 069 101 and EP-A 1 134 271, heptene mixtures, e.g. from the acid- or nickel-catalyzed codimerization of propene and butene, octene mixtures from the dimerization of butenes, for example as described in U.S. Pat. No. 5,849,972, nonene mixtures, e.g. from the acid-catalyzed trimerization of propene, decene mixtures, e.g. from the acid-catalyzed dimerization of pentenes, undecene mixtures, e.g. from the codimerization of pentenes and hexenes, dodecene mixtures, e.g. from the acid-catalyzed tetramerization of propene, the trimerization of butene mixtures, e.g. as described in U.S. Pat. No. 5,849,972, and/or the dimerization of hexene mixtures, e.g. as described in WO 00/53546, hexadecene mixtures, e.g. from the tetramerization of butene mixtures, e.g. as described in U.S. Pat. No. 5,849,972, octadecene mixtures, e.g. from the dimerization of nonene mixtures, and/or eicosene mixtures from the dimerization of decene mixtures or the tetramerization of pentene mixtures. It goes without saying that it is also possible to use compositions comprising olefins having different numbers of carbon atoms in the process of the present invention. Such olefin compositions having different numbers of carbon atoms can be obtained, for example, by metathesis of butenes as described in EP-A 1 134 271 and EP-A 1 069 101 or via the SHOP process or the Fischer-Tropsch process. A compendium of various suitable processes for preparing compositions comprising higher olefins may be found, for example, in Weissermel, Arpe: Industrielle Organische Chemie, pages 82-99, 5th edition, Wiley-VCH, Weinheim 1998. The aldehydes which can be obtained according to the present invention from these olefin compositions are suitable, for example, as starting materials for preparing plasticizer and surfactant alcohols which can be obtained therefrom either directly by, for example, hydrogenation of the aldehyde to the alcohol or via the steps of aldolization and hydrogenation, for example 2-propylheptanol which can be produced by aldolization of valeraldehyde (obtained by hydroformylation of raffinate II) and subsequent hydrogenation of the aldolization product 2-propylheptenal.

Merely by way of example for the purposes of illustration without any intention of giving an exhaustive list, some representative olefinic compounds which can occur in such olefin compositions are listed below:

butenes such as 1-butene, 2-butene and isobutene, pentenes such as 1-pentene, 2-pentene, 2-methyl-1-butene and 2-methyl-2-butene, hexenes such as 1-hexene, 2-hexene, 3-hexene, 2-methyl-1-pentene, 2-methyl-2-pentene, 3-methyl-2-pentene and 3-methyl-1-pentene, heptenes such as 1-heptene, 2-heptene, 3-heptene and the various isomers of methylhexene, octenes such as 1-octene, 2-octene, 3-octene, 4-octene and also branched octenes having an internal or terminal double bond, nonenes such as 1-nonene, 2-nonene, 3-nonene, 4-nonene and also branched nonenes having an internal or terminal double bond, decenes such as 1-decene, 2-decene, 3-decene, 4-decene, 5-decene and also branched decenes having an internal or terminal double bond, undecenes such as 1-undecene, 2-undecene, 3-undecene, 4-undecene, 5-undecene and also branched undecenes having an internal or terminal double bond, dodecenes such as 1-dodecene, 2-dodecene, 3-dodecene, 4-dodecene, 5-dodecene, 6-dodecene and also branched dodecenes having an internal or terminal double bond. Tetradecenes, pentadecenes, hexadecenes, heptadecenes, octadecenes, nonadecenes and eicosenes are likewise suitable.

The olefin compositions which can be used in the process of the present invention can also comprise diolefins, for example α-ω-diolefins such as 1,3-butadiene, 1,4-pentadiene, 1,5-hexadiene, 1,6-heptadiene, 1,7-octadiene, 1,8-nonadiene or 1,9-decadiene, and also diolefins having both internal and terminal double bonds, e.g. 1,3-pentadiene, 1,3-hexadiene, 1,4-hexadiene, 1,3-heptadiene, 1,4-heptadiene, 1,5-heptadiene, 1,3-octadiene, 1,4-octadiene, 1,5-octadiene, 1,6-octadiene, 1,3-nonadiene, 1,4-nonadiene, 1,5-nonadiene, 1,6-nonadiene, 1,7-nonadiene, 1,3-decadiene, 1,4-decadiene, 1,5-decadiene, 1,6-decadiene, 1,7-decadiene, 1,8-decadiene.

The hydroformylation process of the present invention is carried out using rhodium catalysts which are dissolved homogeneously in the reaction medium and are complexed with a phosphorous-containing ligand which is capable of isomerizing and hydroformylating olefins having internal double bonds under the reaction conditions according to the present invention and has only a relatively small tendency to isomerize terminal double bonds to internal double bonds under the reaction conditions according to the present invention. The ligand is advantageously used in an excess over the rhodium, generally at a ligand/Rh molar ratio of from 2 to 300, preferably from 2 to 20 and particularly preferably from 2 to 10.

The rhodium concentration in the liquid reaction mixture is generally from 10 to 500 ppm by weight, preferably from 30 to 350 ppm by weight and particularly preferably from 50 to 300 ppm by weight. As rhodium source, it is possible to use, for example, rhodium salts such as rhodium acetate, rhodium chloride or rhodium nitrate, rhodium complexes such as rhodium acetylacetonate and/or rhodium carbonyl compounds such as $Rh(CO)_2acac$, $Rh_4(CO)_{12}$ or $Rh_6(CO)_{16}$ (acac: acetylacetonate). The type of rhodium source used is generally not critical to the result of the process of the present invention.

To carry out the hydroformylation, the rhodium compound serving as rhodium source is generally dissolved or suspended in the reaction mixture, and the ligand to be used is dealt with similarly. The hydroformylation-active rhodium complex is then formed in situ in the hydroformylation reactor under the conditions of the hydroformylation reaction, i.e. by reaction of carbon monoxide and hydrogen with the rhodium compound complexed with the phosphorus-containing ligand. It goes without saying that preformed rhodium catalyst complexes can also be added to the reaction mixture.

The process of the present invention is carried out in a homogeneous phase, i.e. the olefin to be hydroformylated, the rhodium hydroformylation catalyst dissolved homogeneously in the reaction mixture, free ligand and also the aldehyde formed are present in a liquid phase, i.e. the process of the present invention does not provide for hydroformylation in two liquid phases which are present side-by-side.

The hydroformylation process of the present invention can advantageously be carried out in the presence of solvents. As solvents, preference is given to using the aldehydes which are formed in the hydroformylation of the respective olefins and also their higher-boiling downstream reaction products, i.e. the products of aldol condensation. Solvents which are likewise suitable are aromatics such as toluene and xylenes, hydrocarbons or mixtures of hydrocarbons which can also serve for diluting the above-mentioned aldehydes and the downstream products of the aldehydes. Further possible solvents are esters of aliphatic carboxylic acids with alkanols, for example ethyl acetate or Texanol®, ethers such as tert-butyl methyl ether and tetrahydrofuran. In the case of ligands which are sufficiently hydrophilic, it is also possible to use alcohols such as methanol, ethanol, n-propanol, isopropanol, n-butanol, isobutanol, ketones such as acetone and methyl ethyl ketone etc. "Ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)phosphonium salts, e.g. the tetrafluoroborates, acetates, tetrachloroaluminates, hexafluorophosphates, chlorides and tosylates.

The process of the present invention is advantageously carried out using the liquid discharge method. Here, the liquid hydroformylation mixture is continuously taken off from the hydroformylation reactor of a first reaction zone and fed to the hydroformylation reactor of the next reaction zone. Since the downstream reaction zone is operated at a lower total pressure than the preceding zone, the hydroformylation product mixture from the preceding reaction zone can advantageously be depressurized into the hydroformylation reactor of the downstream reaction zone. In general, the hydroformylation product mixture from a first reaction zone is not worked up before it enters the following reaction zone. The downstream reaction zone is operated under the selected reaction conditions which are different from the reaction conditions of the preceding reaction zone. The liquid hydroformylation mixture is generally taken off continuously from the hydroformylation reactor in this downstream reaction zone and is either depressurized into a depressurization vessel in which the pressure is generally from 1 to 35 bar lower, preferably from 3 to 10 bar lower, than the pressure in the hydroformylation reactor to remove gases dissolved therein, e.g. unreacted $CO/H_2$ mixture, or is, if desired, fed to a further downstream reaction zone, as described. The gases liberated in the pressurization vessel, in particular unreacted $CO/H_2$ mixture, can, if desired, be recirculated to one of the preceding reaction zones in order to be reacted further, in which case it can be advantageous to subject this gaseous recycle stream to scrubbing or intermediate condensation in a heat exchanger to remove entrained aldehydes and/or olefins or to discharge a substream of this recycle stream so as to avoid accumulation of inert gases in the reactor. The liquid hydroformylation mixture remaining in the depressurization vessel, which comprises the hydroformylation product, olefins dissolved therein, high boilers, the catalyst and free ligands, can subsequently be passed to a degassing column to recover unreacted olefins. The bottoms from the degassing column, which comprise the hydroformylation product, high boilers, catalyst and free ligands, can subsequently be passed to a distillation column where the hydroformylation product is separated off from the high boilers, the catalyst and free ligand and can be used further, while the high boilers, the catalyst and free ligand are, if desired after concentrating the stream and discharging a substream in order to avoid buildup of high boilers in the reactor, advantageously recirculated to the reactor of one of the preceding reaction zones, preferably the first reaction zone. The aldehyde product can be worked up by various methods of the prior art, for example by the process described in U.S. Pat. No. 4,148,830, U.S. Pat. No. 6,100,432 or WO 01/58844.

As catalysts which can isomerize double bonds, preference is given, according to the present invention, to complexes of rhodium with chelating organophosphoramidite or organophosphite or organophosphonite ligands. In these ligands, one or more of the phosphorus atoms can be replaced by arsenic and/or antimony atoms, but preference is given to using phosphorus-containing ligands.

Isomerizing hydroformylation catalysts which are suitable for use in the process of the present invention are, for example, rhodium complexes with phosphoramidite ligands of the formula I,

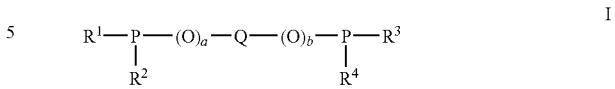

where
Q is a bridging group of the formula

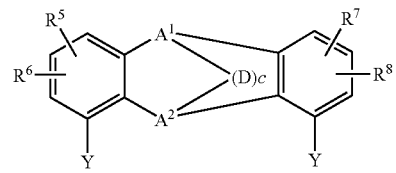

where
$A^1$ and $A^2$ are each, independently of one another, O, S, $SiR^aR^b$, $NR^c$ or $CR^dR^e$, where
$R^a$, $R^b$ and $R^c$ are each, independently of one another, hydrogen, alkyl, cycloalkyl, heterocycloalkyl, aryl or hetaryl,
$R^d$ and $R^e$ are each, independently of one another, hydrogen, alkyl, cycloalkyl, heterocycloalkyl, aryl or hetaryl or together with the carbon atom to which they are bound form a cycloalkylidene group having from 4 to 12 carbon atoms or the group $R^d$ together with a further group $R^d$ or the group $R^e$ together with a further group $R^e$ forms an intramolecular bridging group D,
D is a divalent bridging group selected from among the groups

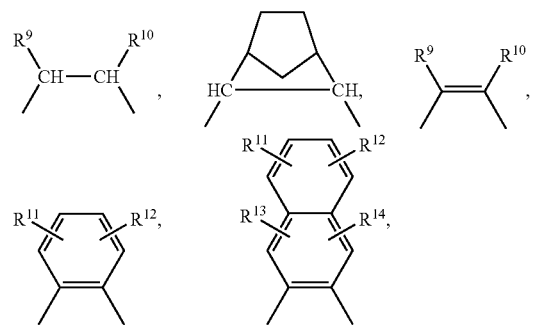

where
$R^9$ and $R^{10}$ are each, independently of one another, hydrogen, alkyl, cycloalkyl, aryl, halogen, trifluoromethyl, carboxyl, carboxylate or cyano or are joined to one another to form a $C_3$- to $C_4$-alkylene bridge,
$R^{11}$, $R^{12}$, $R^{13}$ and $R^{14}$ are each, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, acyl or nitro,
c is 0 or 1,
Y is a chemical bond,
$R^5$, $R^6$, $R^7$ and $R^8$ are each, independently of one another, hydrogen, alkyl, cycloalkyl, heterocycloalkyl, aryl, hetaryl, $COOR^f$, $COO^-M^+$, $SO_3R^f$, $SO^-_3M^+$, $NE^1E^2$, $NE^1E^2E^{3+}X^-$, alkylene-$NE^1E^2E^{3+}X^-$, $OR^f$, $SR^f$, $(CHR^gCH_2O)_xR^f$, $(CH_2N(E^1))_xR^f$, $(CH_2CH_2N(E^1))_xR^f$, halogen, trifluoromethyl, nitro, acyl or cyano, where
R$^f$, E$^1$, E$^2$ and E$^3$ are identical or different radicals selected from among hydrogen, alkyl, cycloalkyl and aryl,
R$^g$ is hydrogen, methyl or ethyl,
M$^+$ is a cation,
X$^-$ is an anion and
x is an integer from 1 to 120,
or
R$^5$ and/or R$^7$ together with two adjacent carbon atoms of the benzene ring to which they are bound form a fused ring system having 1, 2 or 3 further rings,
a and b are each, independently of one another, 0 or 1,
P is phosphorus,
and
R$^1$, R$^2$, R$^3$, R$^4$ are each, independently of one another, hetaryl, hetaryloxy, alkyl, alkoxy, aryl, aryloxy, cycloalkyl, cycloalkoxy, heterocycloalkyl, heterocycloalkoxy or an NE$^1$E$^2$ group, with the proviso that R$^1$ and R$^3$ are bound via the nitrogen atom of pyrrole groups bound to the phosphorus atom P or R$^1$ together with R$^2$ and/or R$^3$ together with R$^4$ form a divalent group E which contains at least one pyrrole group bound via the pyrrole nitrogen to the phosphorus atom P and has the formula Py-I—W where
Py is a pyrrole group,
I is a chemical bond or O, S, SiR$^a$R$^b$, NR$^c$ or CR$^h$R$^i$,
W is cycloalkyl, cycloalkoxy, aryl, aryloxy, hetaryl or hetaryloxy,
and
R$^h$ and R$^i$ are each, independently of one another, hydrogen, alkyl, cycloalkyl, heterocycloalkyl, aryl or hetaryl,
or form a bispyrrole group which is bound via the nitrogen atoms to the phosphorus atom P and has the formula Py-I-Py.

Preferred phosphoramidite ligands are ligands of the formula Ia

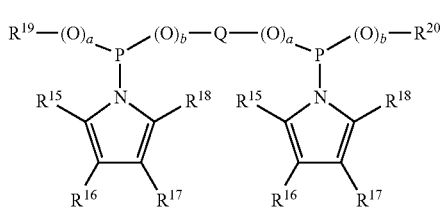

where
R$^{15}$, R$^{16}$, R$^{17}$ and R$^{18}$ are each, independently of one another, hydrogen, alkyl, cycloalkyl, heterocycloalkyl, aryl, hetaryl, W'COOR$^k$, W'COO$^-$M$^+$, W'(SO$_3$)R$^k$, W'(SO$_3$)$^-$M$^+$, W'PO$_3$(R$^k$)(R$^l$), W'(PO$_3$)$_2^-$(M$^+$)$_2$, W'NE$^4$E$^5$, W'(NE$^4$E$^5$E$^6$)$^+$X$^-$, W'OR$^k$, W'SR$^k$, (CHR$^j$CH$_2$O)$_y$R$^k$, (CH$_2$NE$^4$)$_y$R$^k$, (CH$_2$CH$_2$NE$^4$)$_y$R$^k$, halogen, trifluoromethyl, nitro, acyl or cyano,
where
W' is a single bond, a heteroatom or a divalent bridging group having from 1 to 20 bridge atoms,
R$^k$, E$^4$, E$^5$, E$^6$ are identical or different radicals selected from among hydrogen, alkyl, cycloalkyl and aryl,
R$^l$ is hydrogen, methyl or ethyl,
M$^+$ is a cation equivalent,
X$^-$ is an anion equivalent and
y is an integer from 1 to 240,
where two adjacent radicals R$^{15}$, R$^{16}$, R$^{17}$ and R$^{18}$ together with the carbon atoms of the pyrrole ring to which they are bound may also form a fused ring system having 1, 2 or 3 further rings,
with the proviso that at least one of the radicals R$^{15}$, R$^{16}$, R$^{17}$ and R$^{18}$ is not hydrogen and R$^{19}$ and R$^{20}$ are not linked to one another,
R$^{19}$ and R$^{20}$ are each, independenlty of one another, cycloalkyl, heterocycloalkyl, aryl or hetaryl,
a and b are each, independenlty of one another, 0 or 1,
P is a phosphorus atom,
Q is a bridging group of the formula

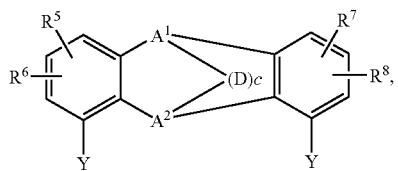

where
A$^1$ and A$^2$ are each, independently of one another, O, S, SiR$^a$R$^b$, NR$^c$ or CR$^d$R$^e$, where
R$^a$, R$^b$ and R$^c$ are each, independently of one another, hydrogen, alkyl, cycloalkyl, heterocycloalkyl, aryl or hetaryl,
R$^d$ and R$^e$ are each, independently of one another, hydrogen, alkyl, cycloalkyl, heterocycloalkyl, aryl or hetaryl or together with the carbon atom to which they are bound form a cycloalkylidene group having from 4 to 12 carbon atoms or the group R$^d$ together with a further group R$^d$ or the group R$^e$ together with a further group R$^e$ forms an intramolecular bridging group D,
D is a divalent bridging group selected from among the groups

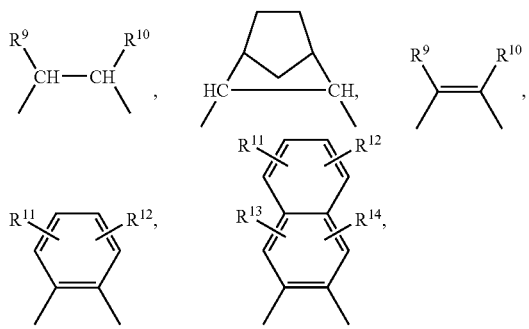

where
R$^9$ and R$^{10}$ are each, independently of one another, hydrogen, alkyl, cycloalkyl, aryl, halogen, trifluoromethyl, carboxyl, carboxylate or cyano or are joined to one another to form a C$_3$- to C$_4$-alkylene bridge,
R$^{11}$, R$^{12}$, R$^{13}$ and R$^{14}$ are each, independently of one another, hydrogen, alkyl, cycloalkyl, aryl, halogen, trifluoromethyl, COOH, carboxylate, cyano, alkoxy, SO$_3$H, sulfonate, NE$^1$E$^2$, alkylene-NE$^1$E$^2$E$^3$$^+$X$^-$, acyl or nitro,
c is 0 or 1,
R$^5$, R$^6$, R$^7$ and R$^8$ are each, independently of one another, hydrogen, alkyl, cycloalkyl, heterocycloalkyl, aryl, hetaryl, $COOR^f$, $COO^-M^+$, $SO_3R^f$, $SO^-_3M^+$, $NE^1E^2$, $NE^1E^2E^{3+}X^-$, alkylene-$NE^1E^2E^{3+}X^-$, $OR^f$, $SR^f$, $(CHR^gCH_2O)_xR^f$, $(CH_2N(E^1))_xR^f$, $(CH_2CH_2N(E^1))_xR^f$, halogen, trifluoromethyl, nitro, acyl or cyano, where $R^f$, $E^1$, $E^2$ and $E^3$ are identical or different radicals selected from among hydrogen, alkyl, cycloalkyl and aryl, $R^g$ is hydrogen, methyl or ethyl,
$M^+$ is a cation,
$X^-$ is an anion and
x is an integer from 1 to 120,
or
$R^5$ and/or $R^7$ together with two adjacent carbon atoms of the benzene ring to which they are bound form a fused ring system having 1, 2 or 3 further rings.

Such ligands are subject matter of WO 02/083695, which is hereby fully incorporated by reference and where the preparation of these ligands is also described. Preferred ligands from this class are, for example, the following compounds, with this listing being merely for the purposes of illustration and not implying any restriction in respect of the ligands which can be employed:

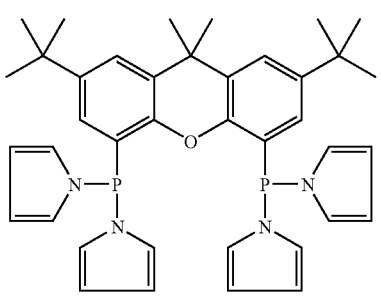

1

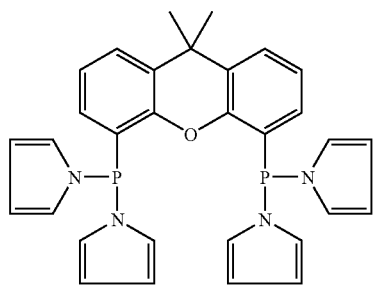

2

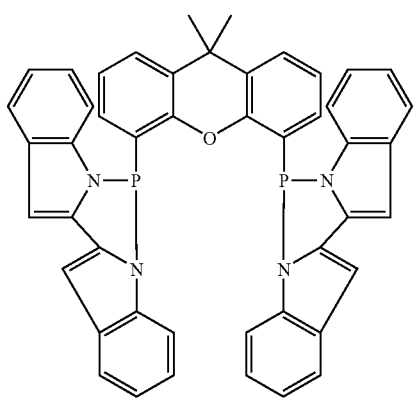

3

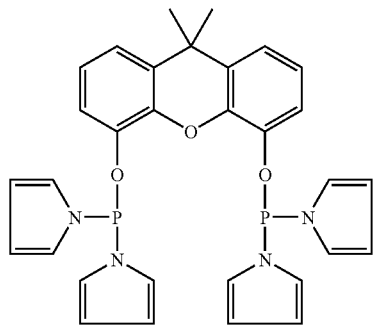
4
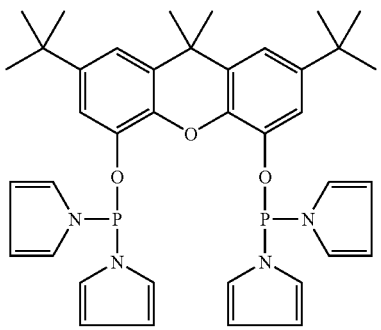
5
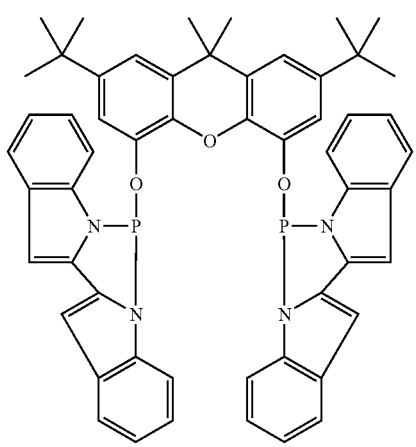
6
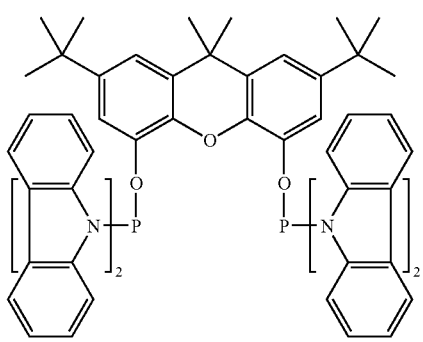
7

-continued
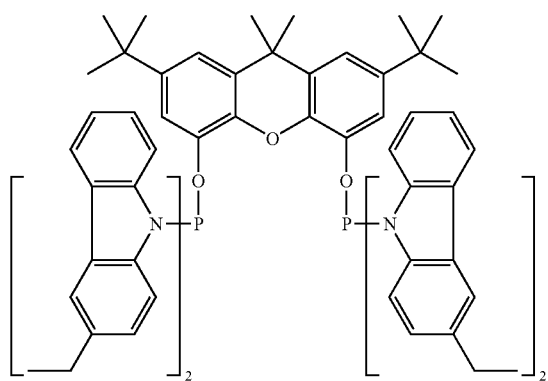
8
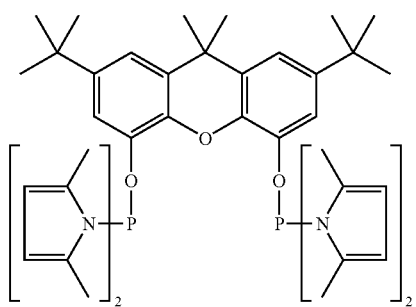
9
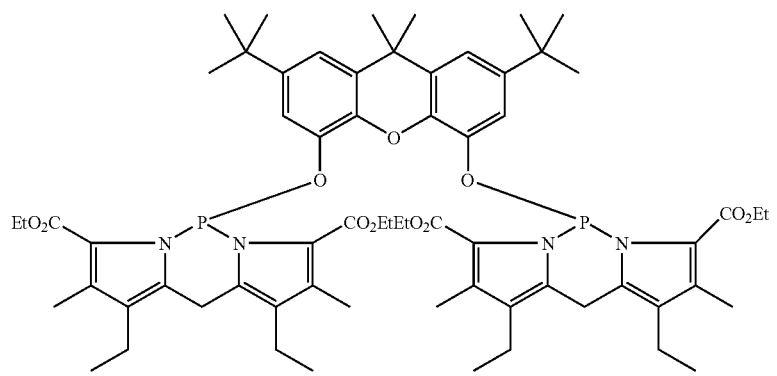
10

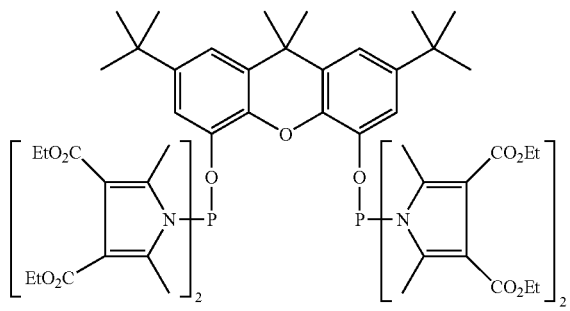
11
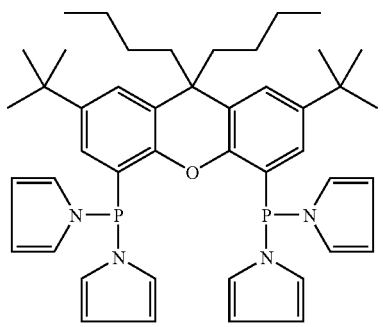
12
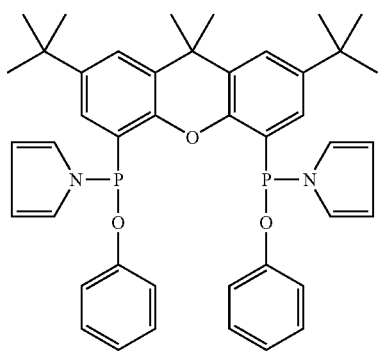
13

-continued
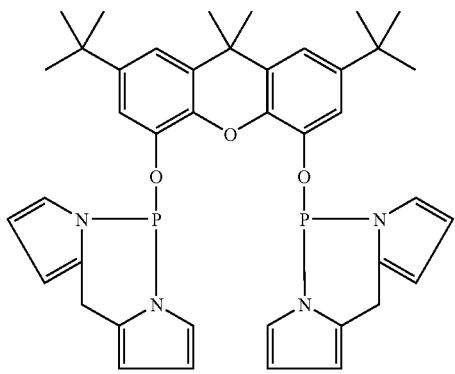
14
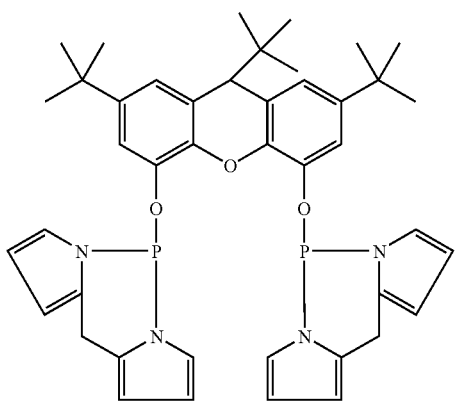
15
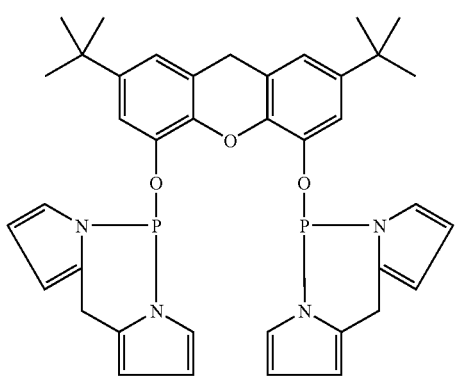
16

17
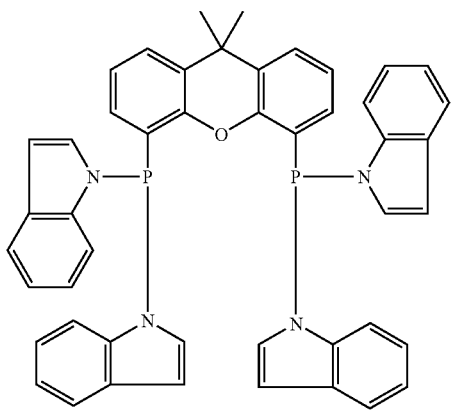
18
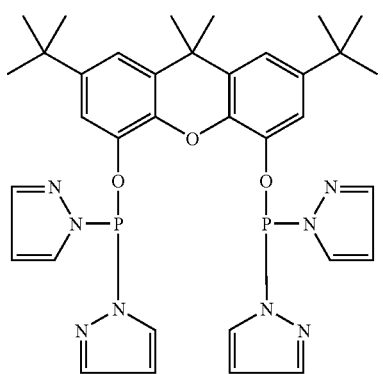
19
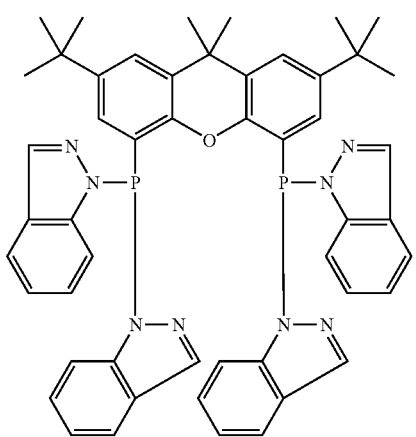

-continued
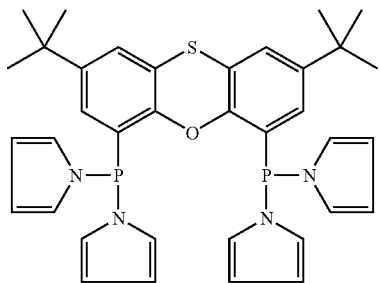
20
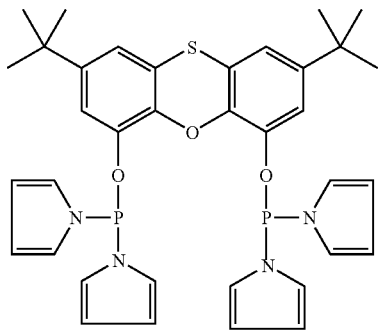
21
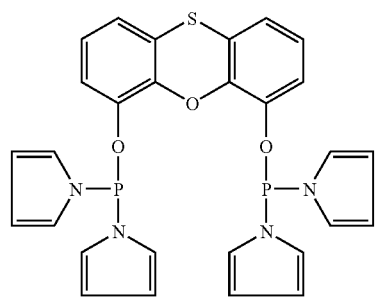
22
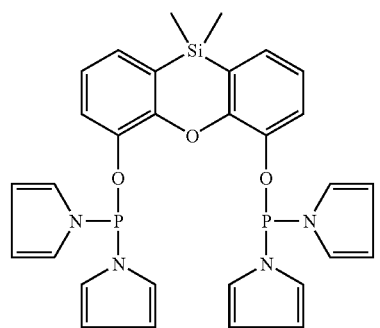
23
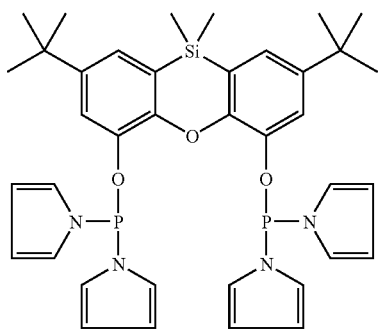
24

-continued
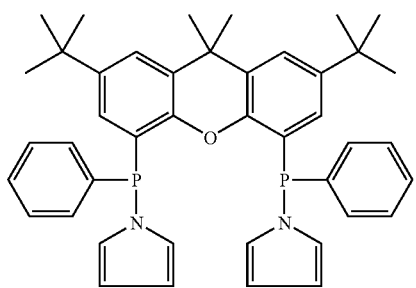
25
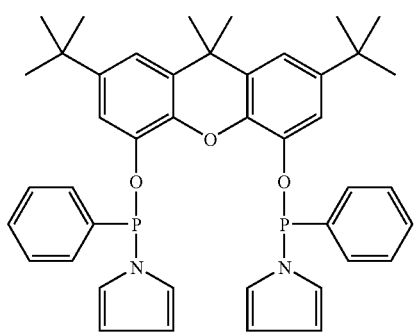
26
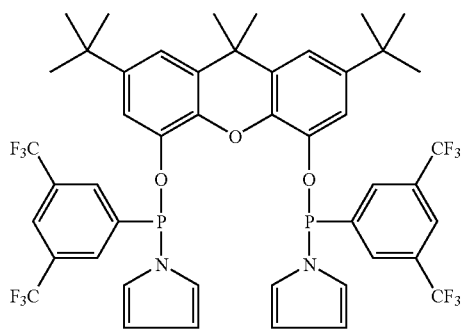
27
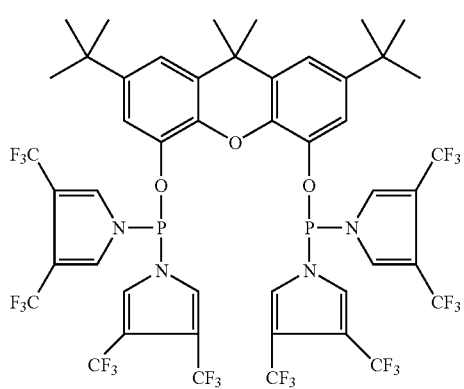
28

-continued
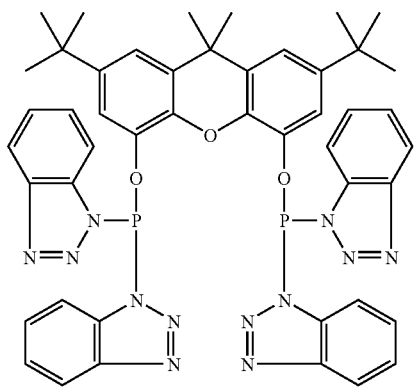
29
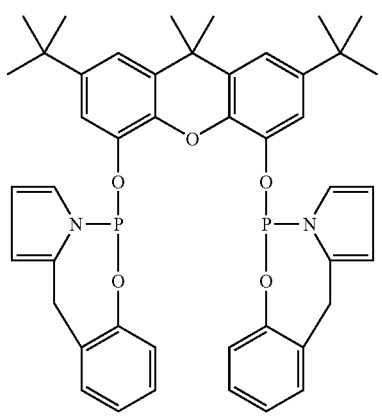
30
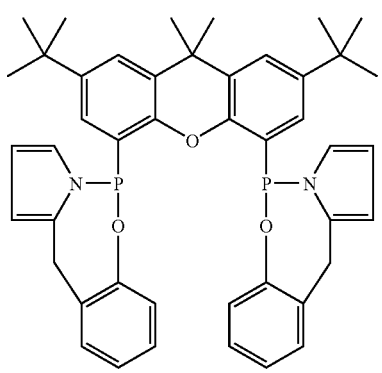
31

-continued
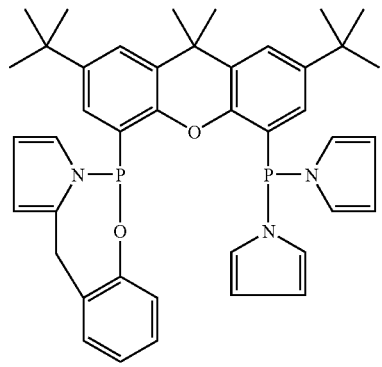
32
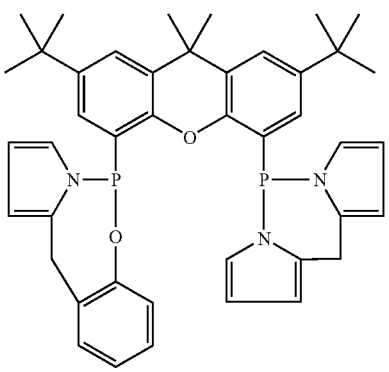
33
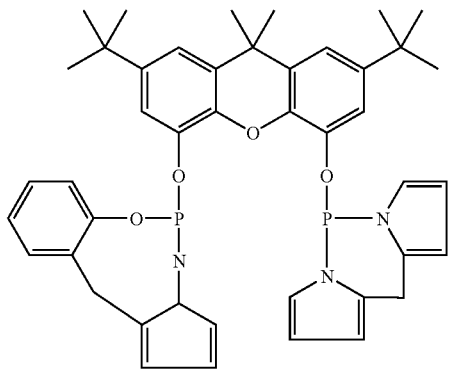
34
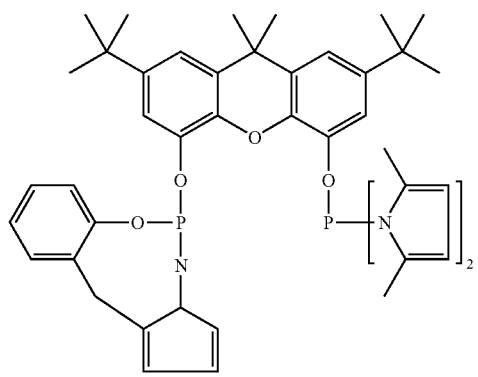
35

-continued
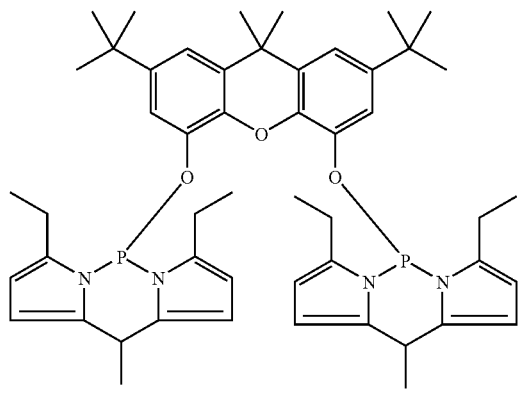
36
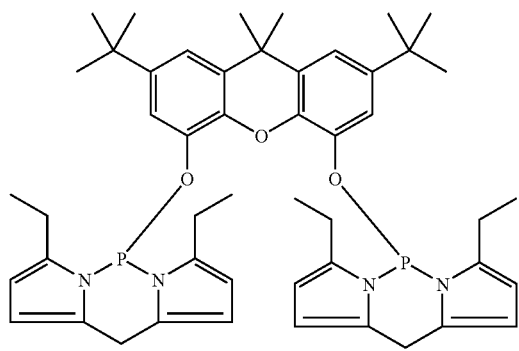
37
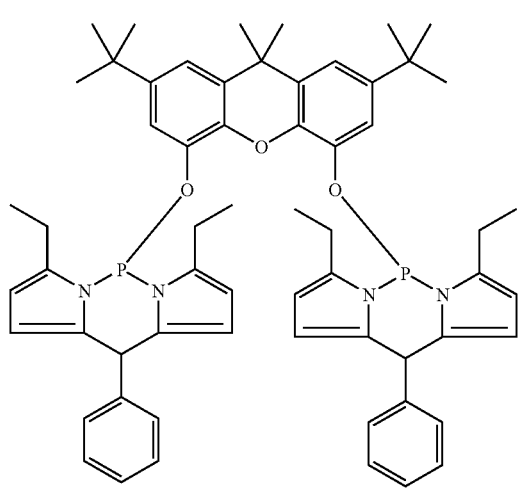
38

-continued
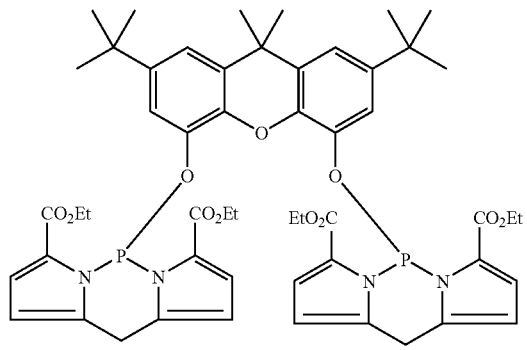
39
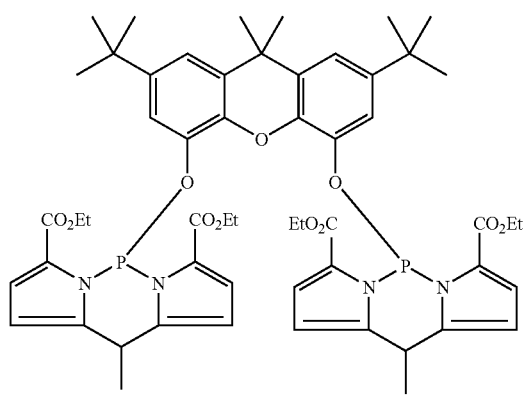
40
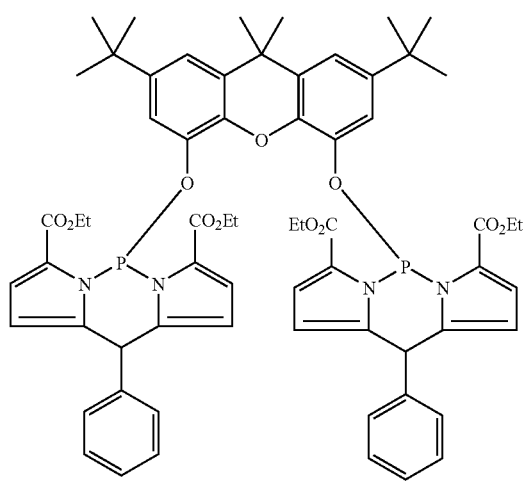
41

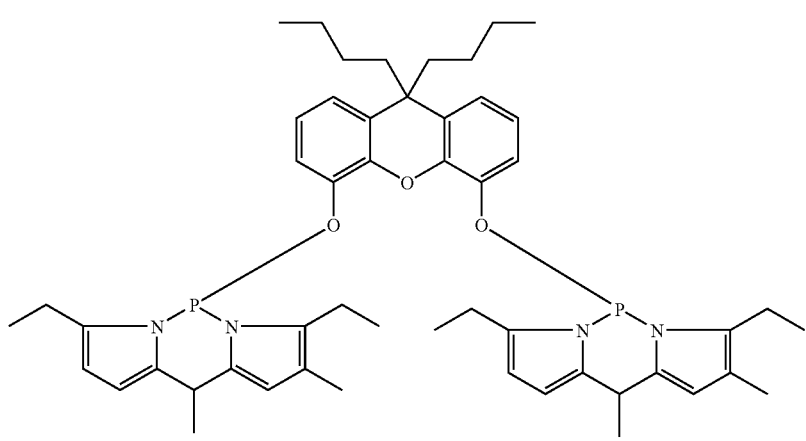
42
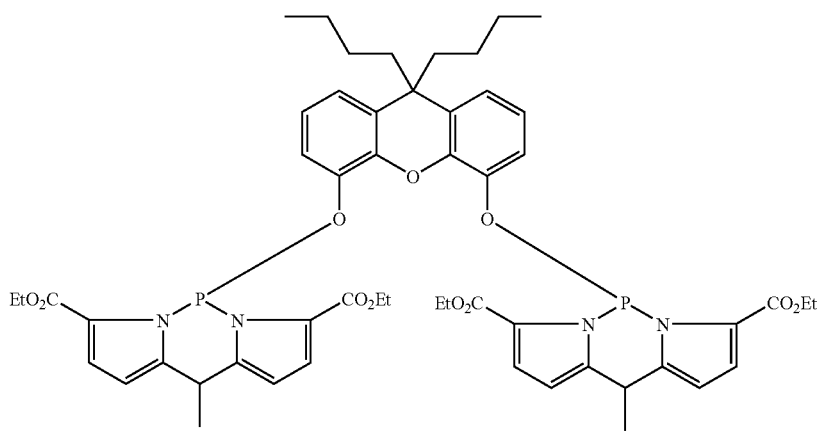
43
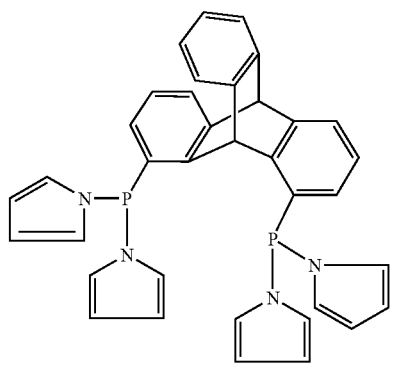
44

-continued
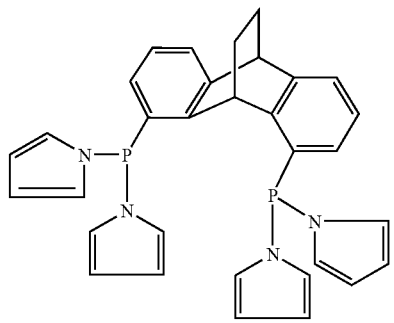
45
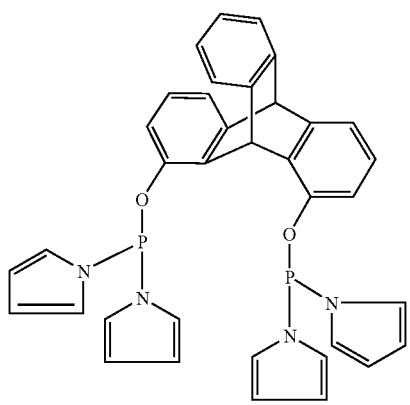
46
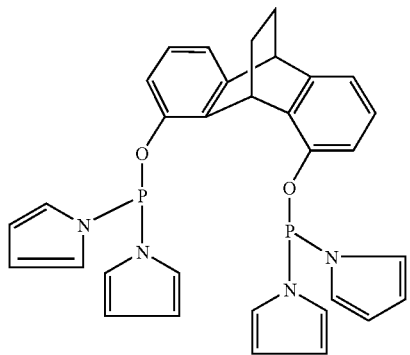
47
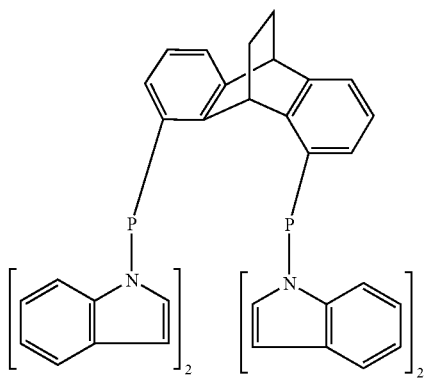
48

-continued
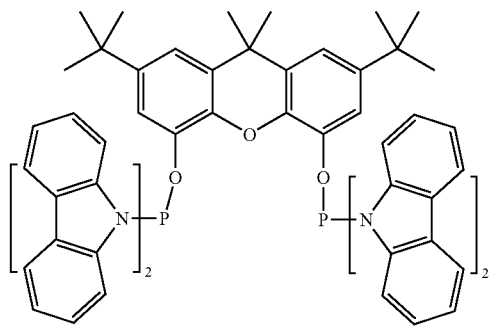
49
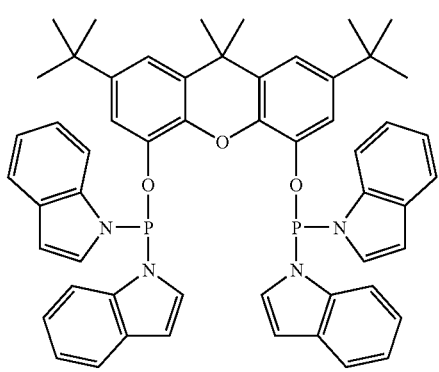
50
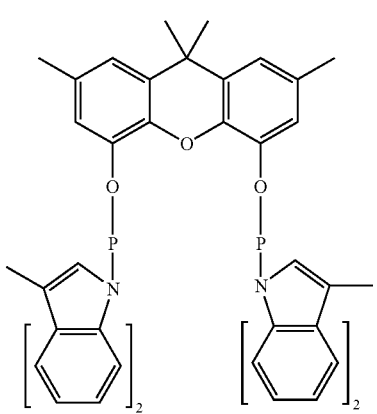
51

52
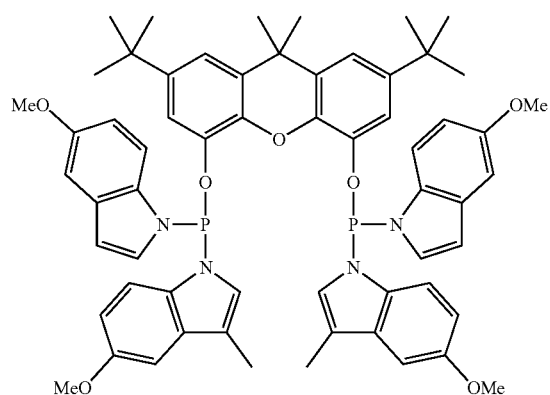
53
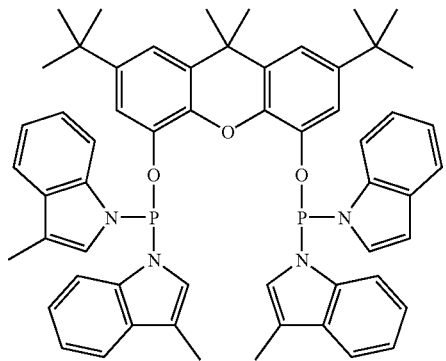
54
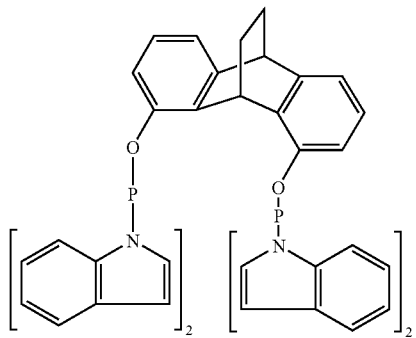
55
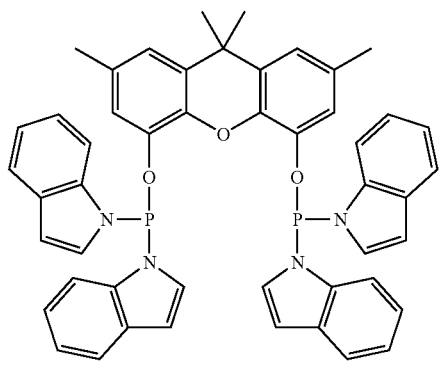

-continued

56

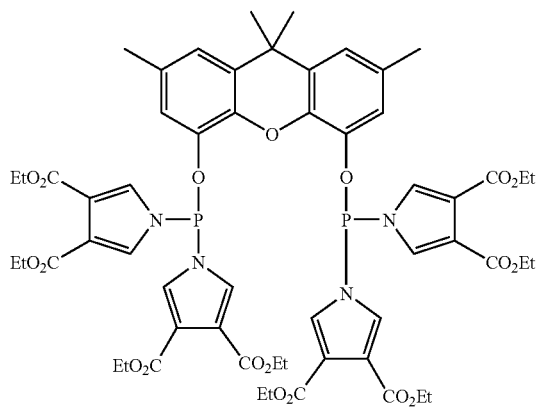

57

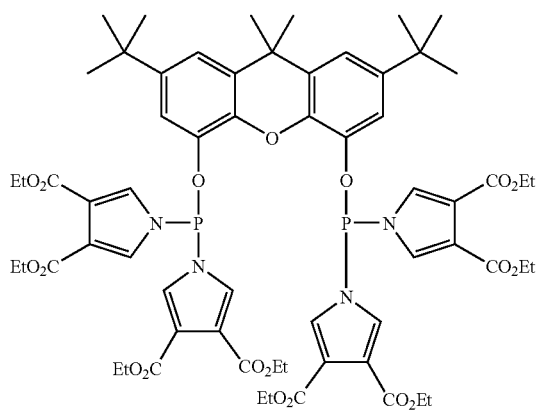

Et: ethyl
Me: methyl

Suitable phosphoramidite ligands for the isomerizing hydroformylation using rhodium complexes as catalysts also include the phosphoramidite ligands described in WO 98/19985 and WO 99/52632, which have 2,2'-dihydroxy-1,1'-biphenylene or 2,2'-dihydroxy-1,1'-binaphthylene bridging groups which bear heteroaryl groups such as pyrrolyl or indolyl groups bound to the phosphorus atom via the nitrogen atom, for example the ligands:

58

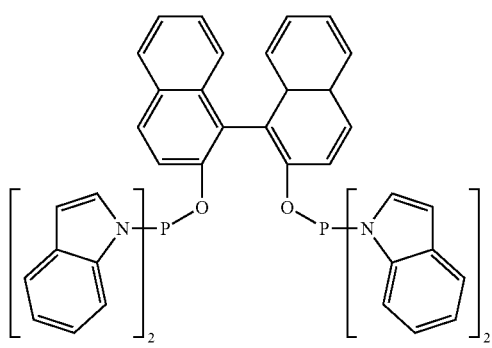

-continued

59

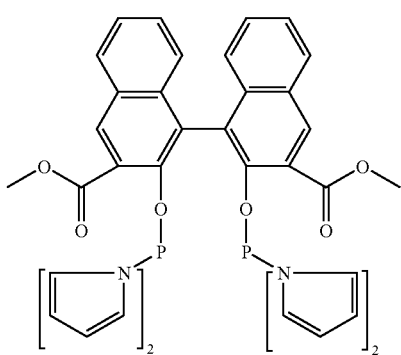

60

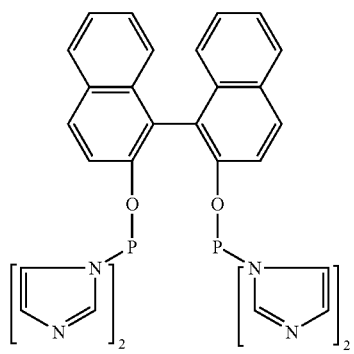

-continued
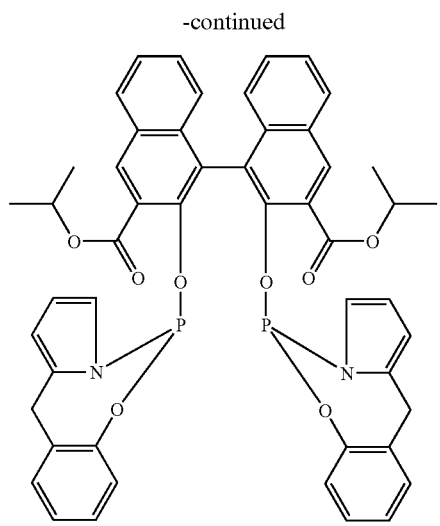
61
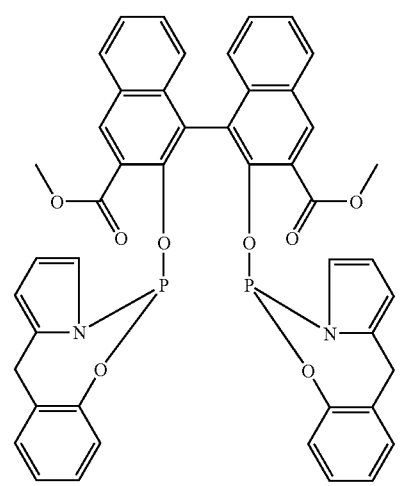
62
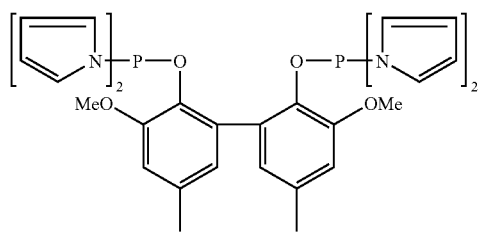
63
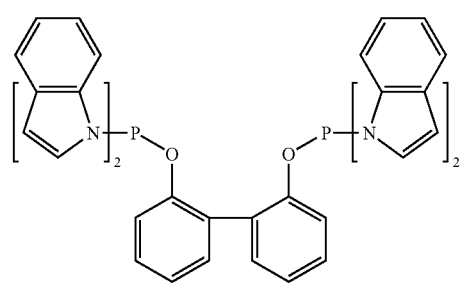
64
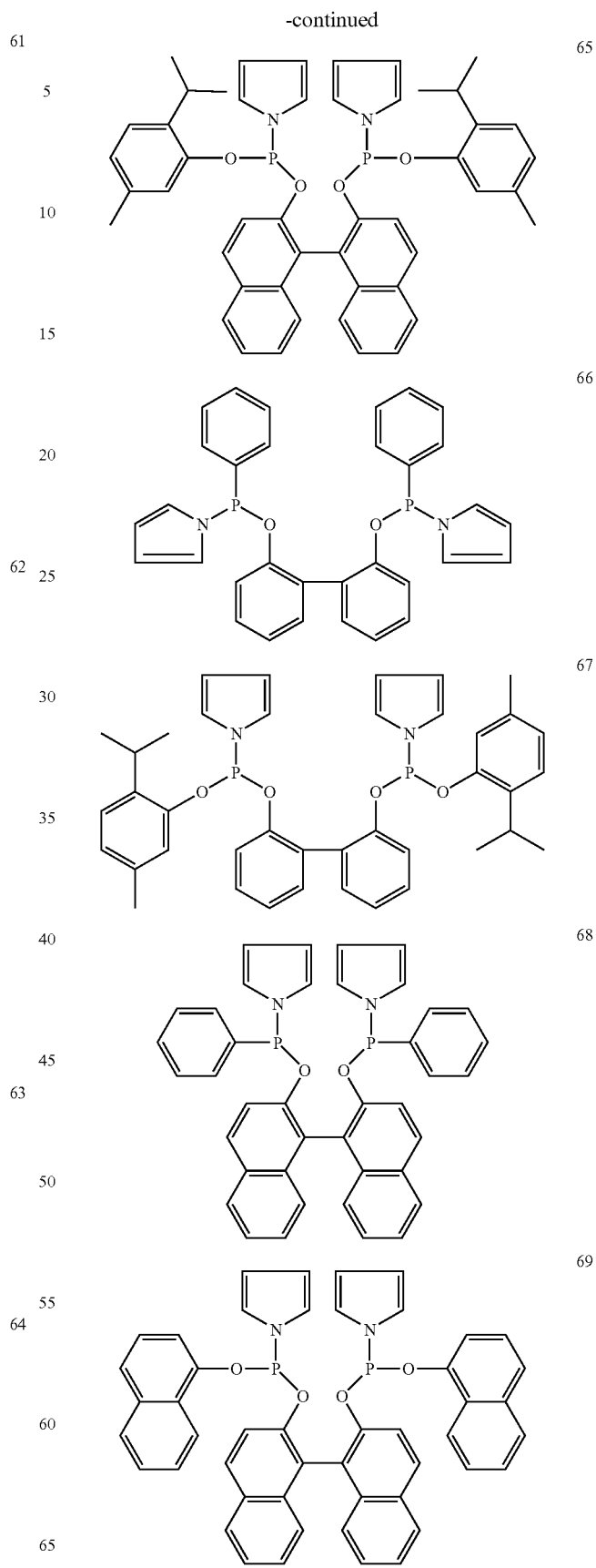

-continued
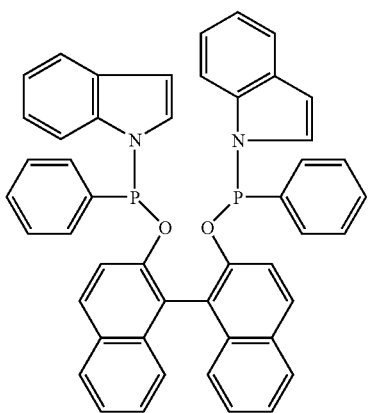
70
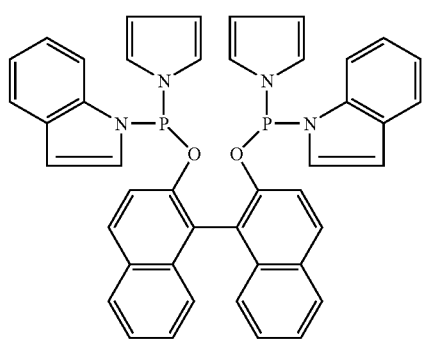
71
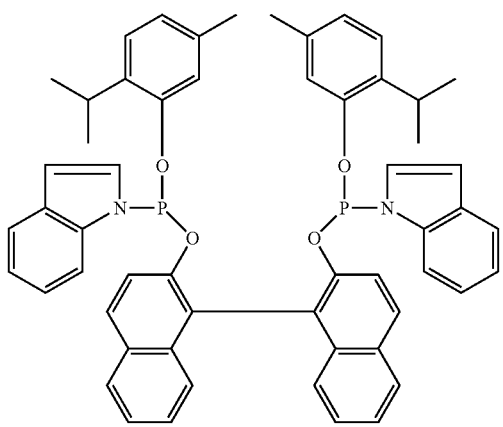
72
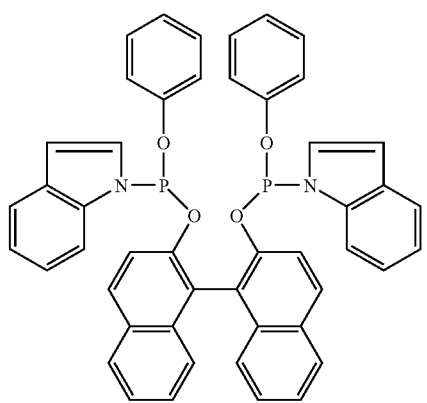
73
-continued
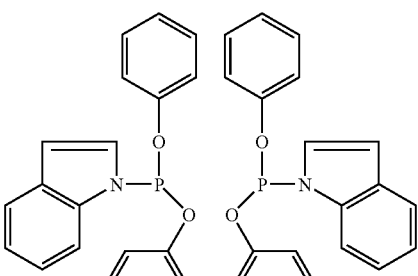
74
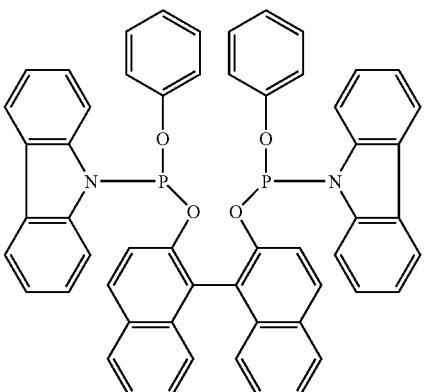
75
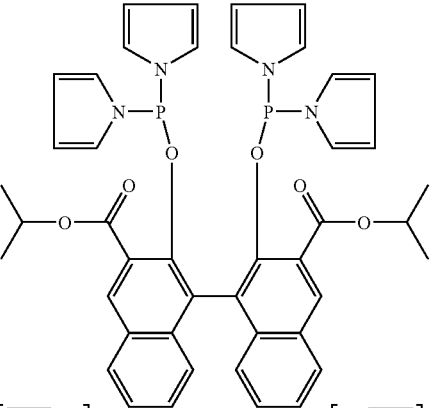
76
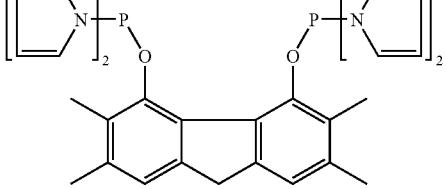
77
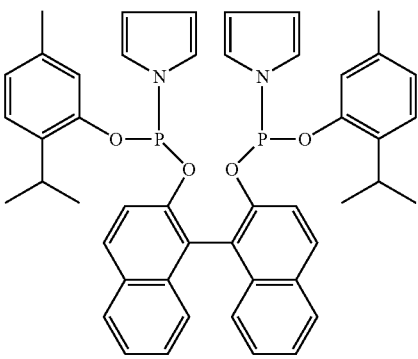
78

Suitable ligands for the isomerizing hydroformylation using rhodium complexes as catalysts also include phosphite and phosphonite ligands as are described, for example, in WO 01/58589. Merely for the purposes of illustration, the following ligands may be mentioned by way of example:

79

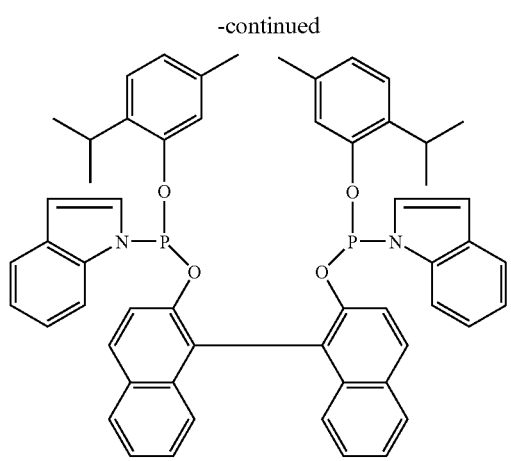

The 1,1'-biphenylene or 1,1'-binaphthylene bridging groups of these ligands can be further bridged via the 1,1 position by a methylene group (CH$_2$—), a 1,1-ethylene group (CH$_3$—CH<) or a 1,1-propylene group (CH$_3$—CH$_2$—HC<).

Suitable phosphonite ligands for the isomerizing hydroformylation using rhodium complexes as catalysts are, inter alia, the ligands described in WO 98/19985, for example:

83

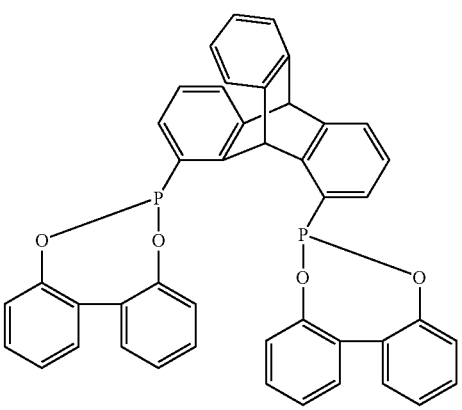

80

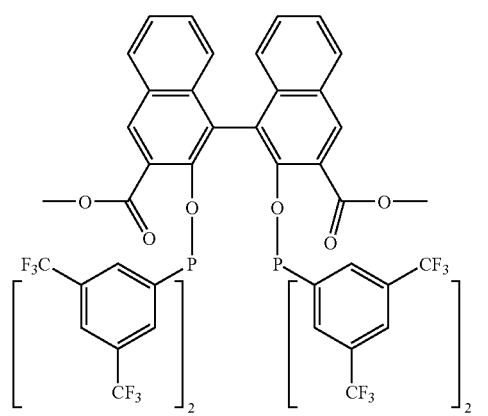

84

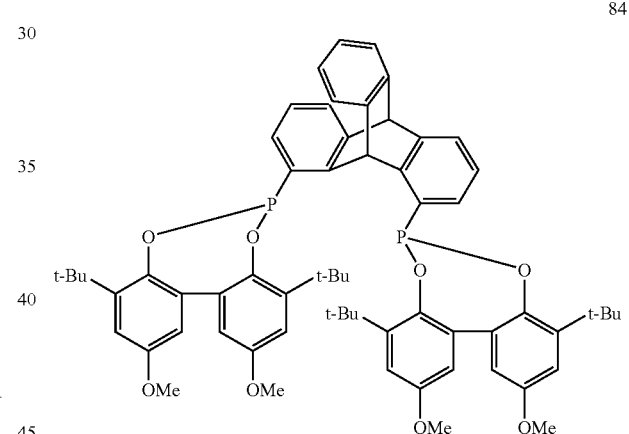

81

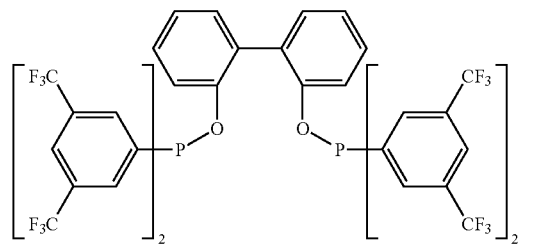

82

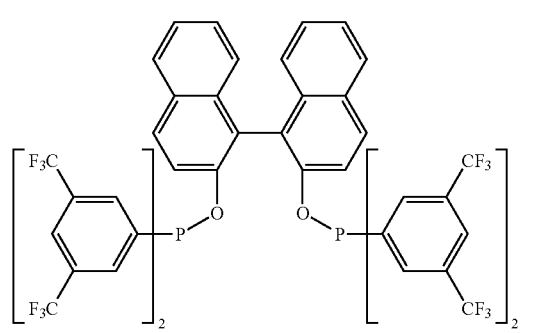

85

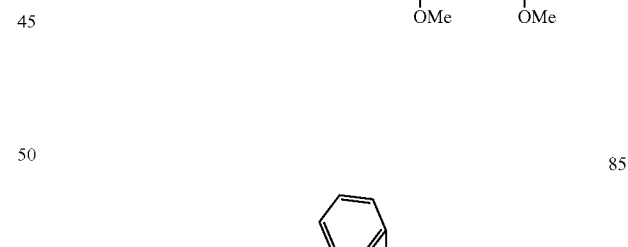

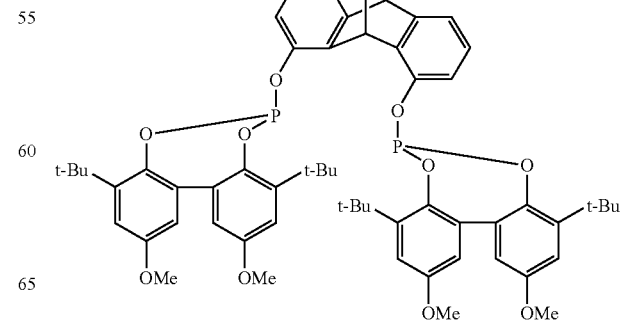

Further well-suited ligands for the isomerizing hydroformylation using rhodium complexes as catalysts are phosphine ligands having the xanthenyl-bisphosphoxanthenyl skeleton, as are described, for example, in WO 02/068371 and EP-A 982314. Merely for the purposes of illustration, some of these ligands are listed below by way of example:
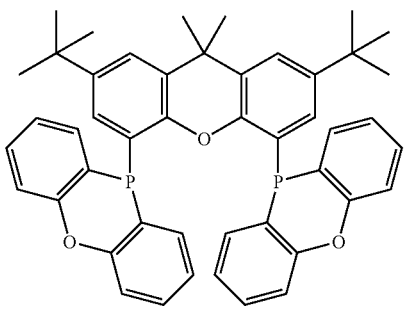
86
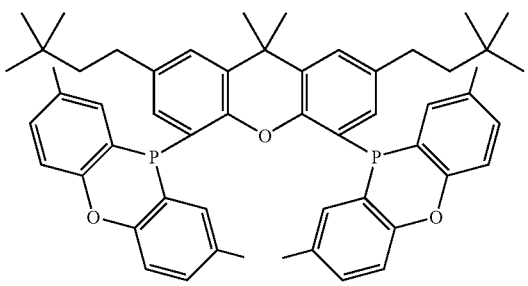
87
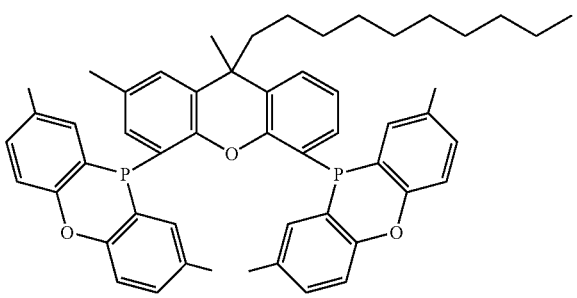
88
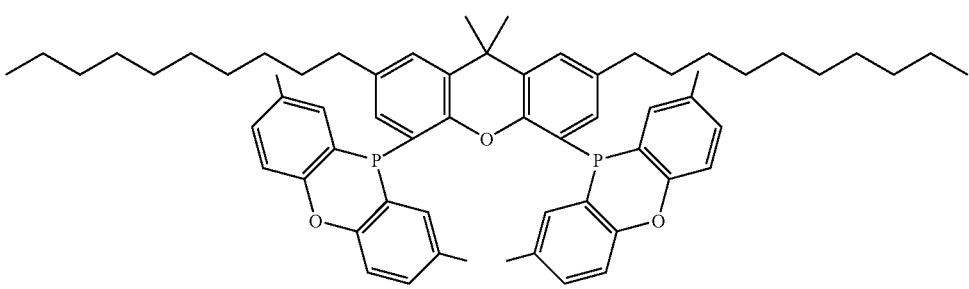
89
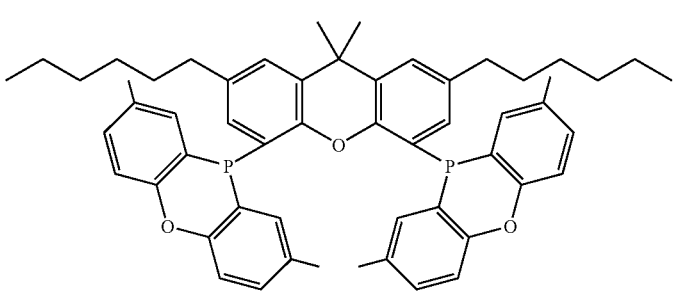
90

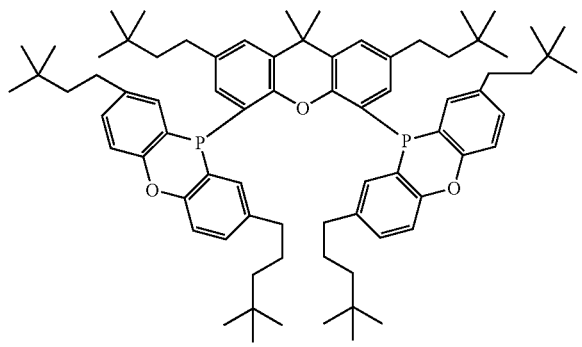

91

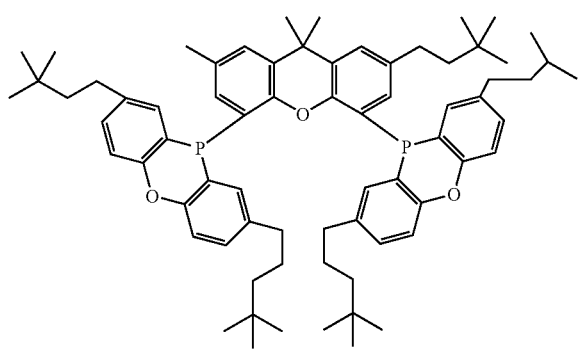

92

Further suitable chelating phosphite ligands for the isomerizing hydroformylation using rhodium complexes of these ligands as catalysts are, for example, ligands of the formulae II, III and IV

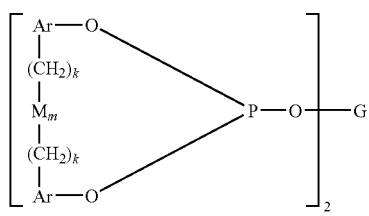

II

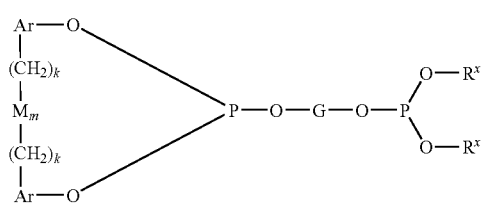

III

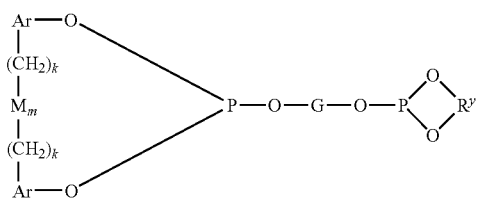

IV where G is a substituted or unsubstituted divalent organic bridging group having from 2 to 40 carbon atoms, M is a divalent bridging group selected from among $-C(R^w)_2-$, $-O-$, $-S-$, $NR^v$, $Si(R^t)_2-$ and $-CO-$, where the groups $R^w$ are identical or different and are each hydrogen, an alkyl group having from 1 to 12 carbon atoms or a phenyl, tolyl or anisyl group, the group $R^v$ is hydrogen or a substituted or unsubstituted hydrocarbon group having from 1 to 12 carbon atoms, the groups $R^t$ are identical or different and are each hydrogen or a methyl group, m is 0 or 1, the groups Ar are identical or different and are each an unsubstituted or substituted aryl group, the index k is 0 or 1, the groups $R^x$ are identical or different and are each an unsubstituted or substituted monovalent alkyl or aryl group and $R^y$ is a divalent organic radical selected from among unsubstituted and substituted alkylene, arylene, arylene-alkylene-arylene and bisarylene groups. Merely for the purposes of illustration without implying any restriction, mention may be made by way of example of the following chelating phosphite ligands which can be used in the process of the present invention:

61
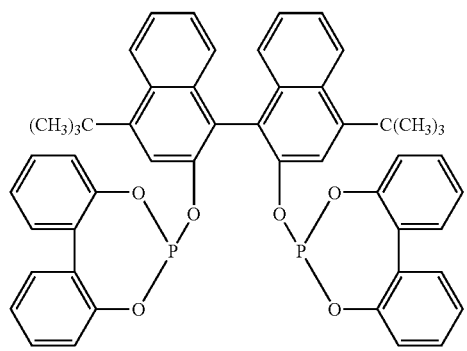
93
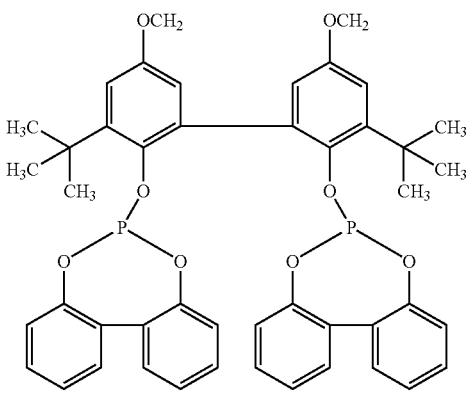
94
95
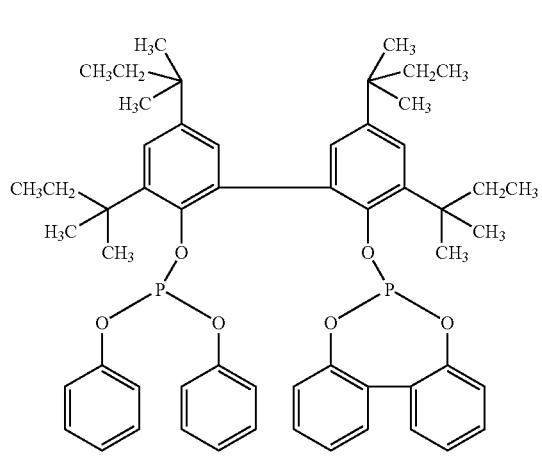
62
96
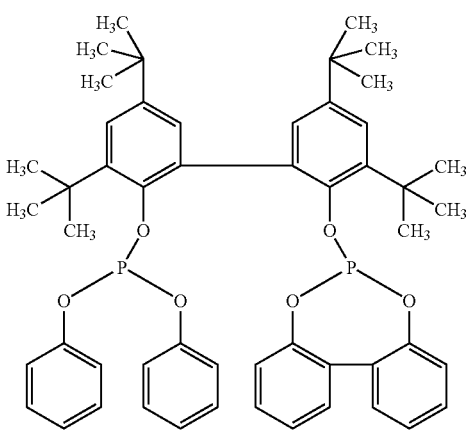
97
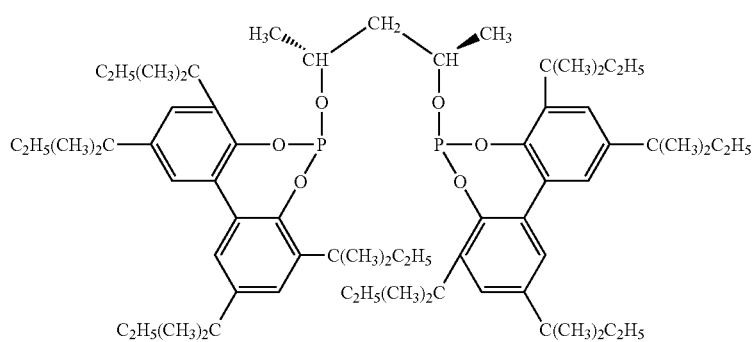
98
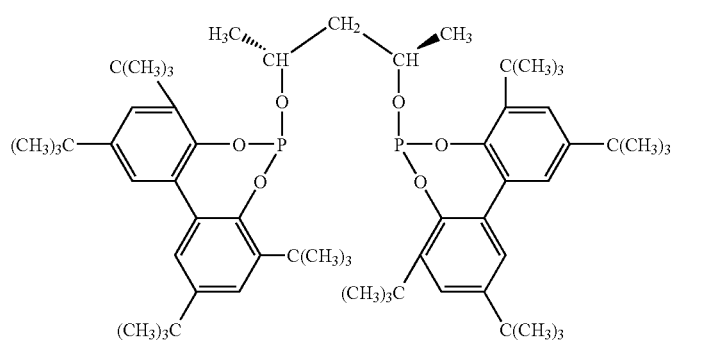

-continued
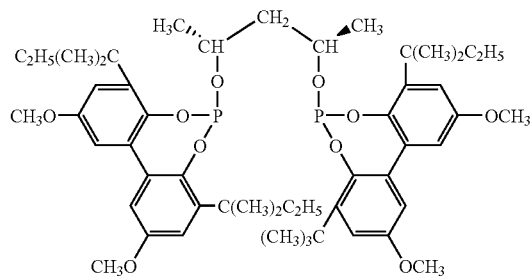 99
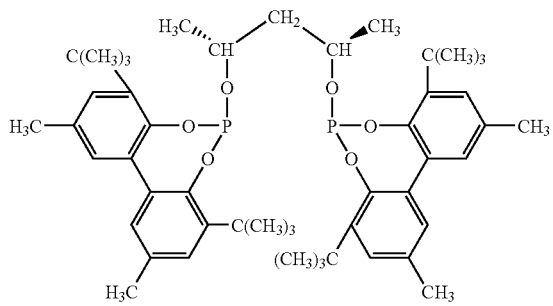 100
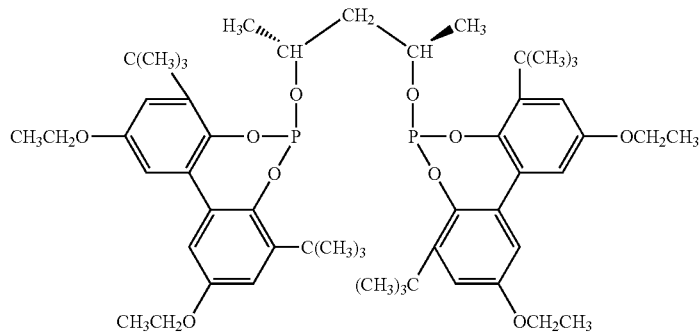 101
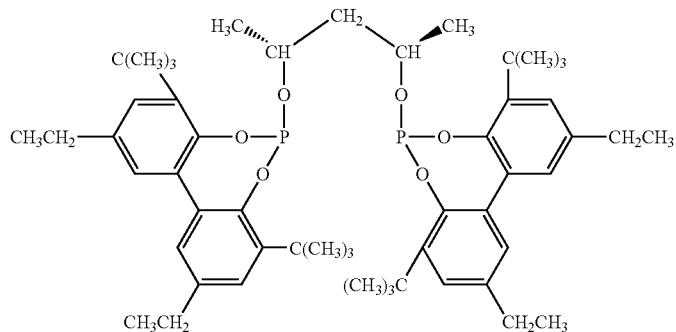 102
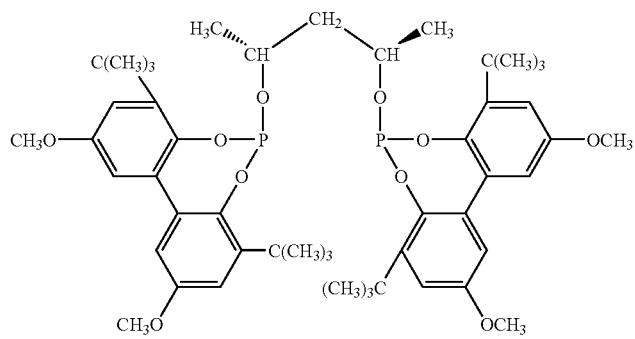 103

104
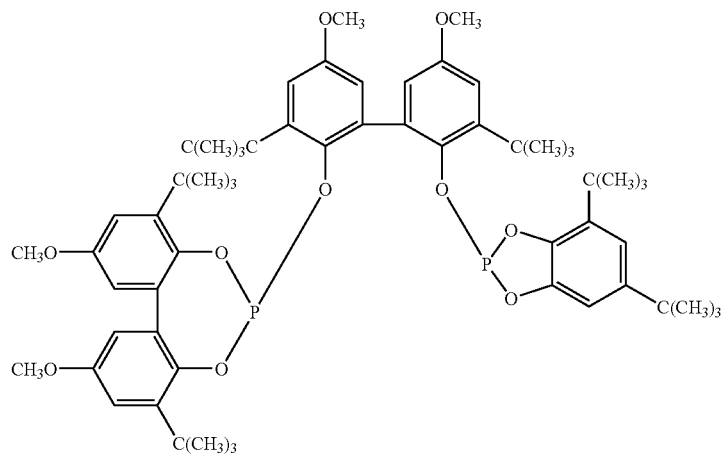
105
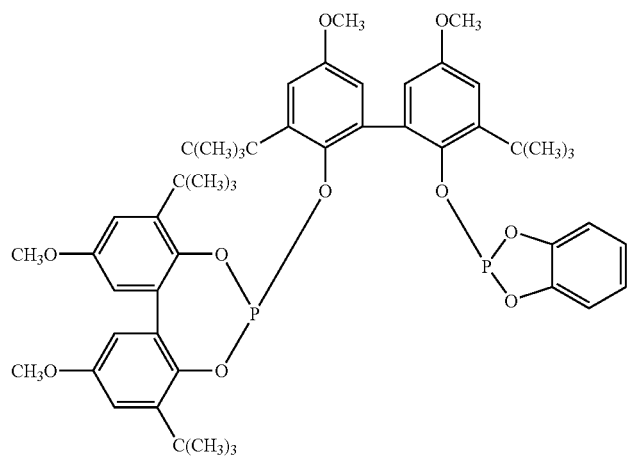
106
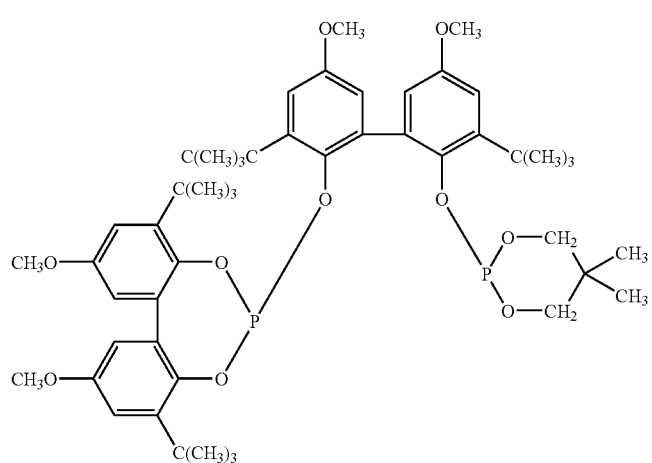

107
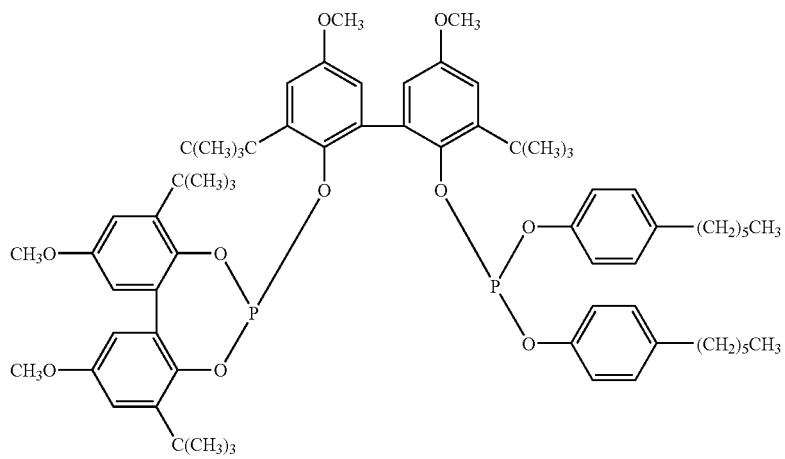
108
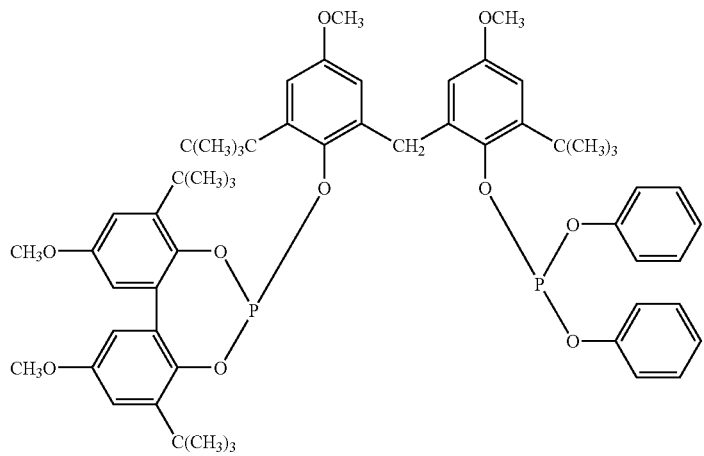
109
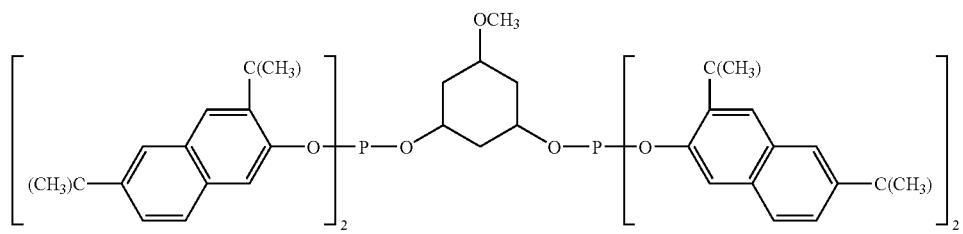
110
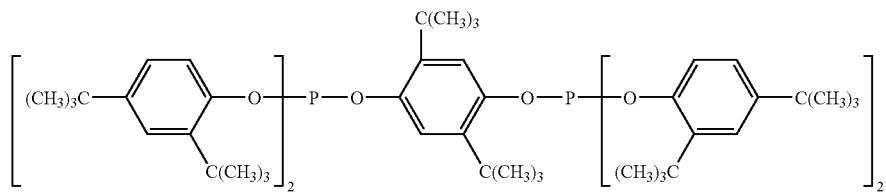
111
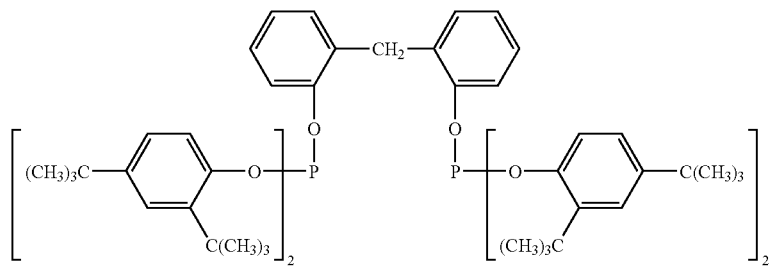

-continued
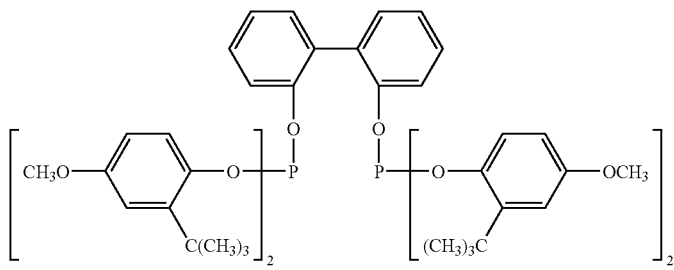
112
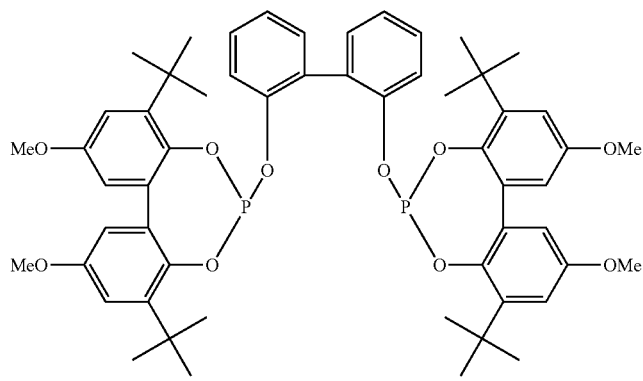
113
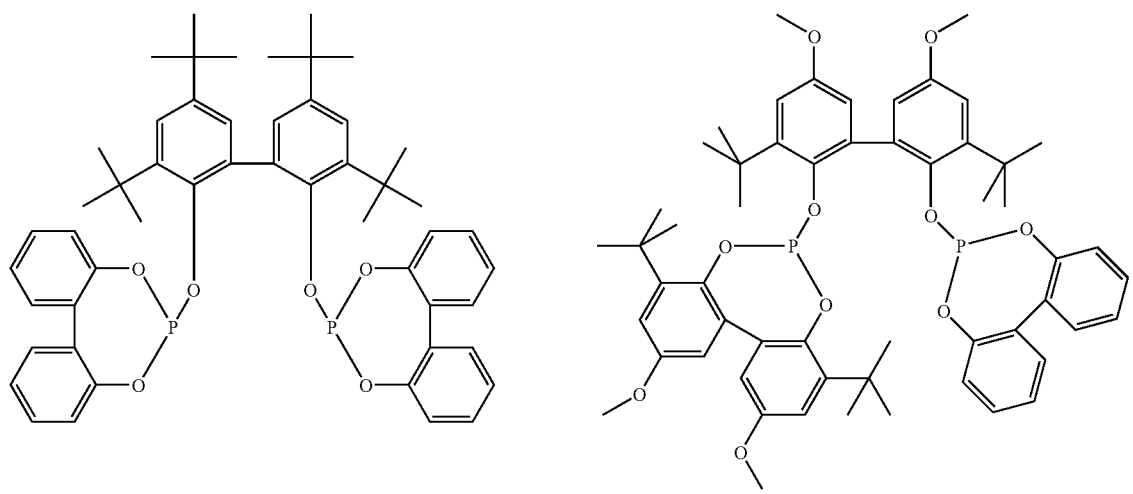
114
115
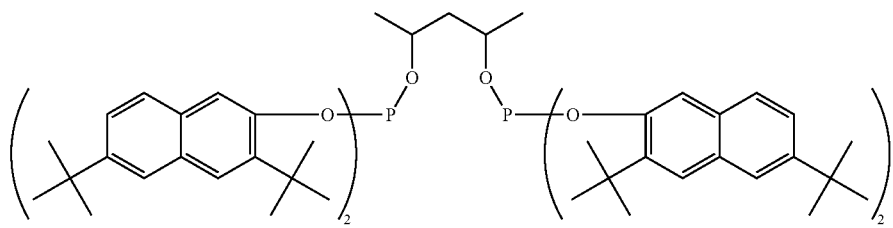
116
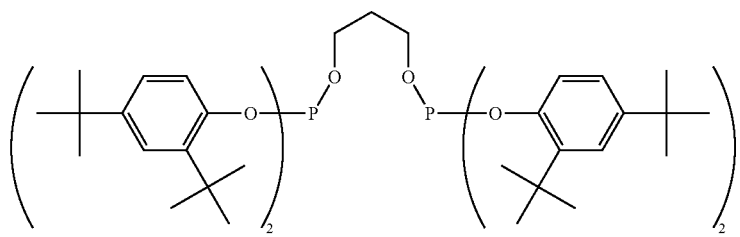
117

-continued
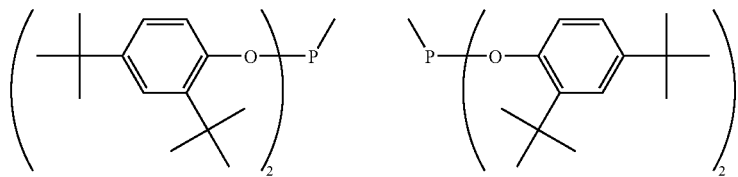
118
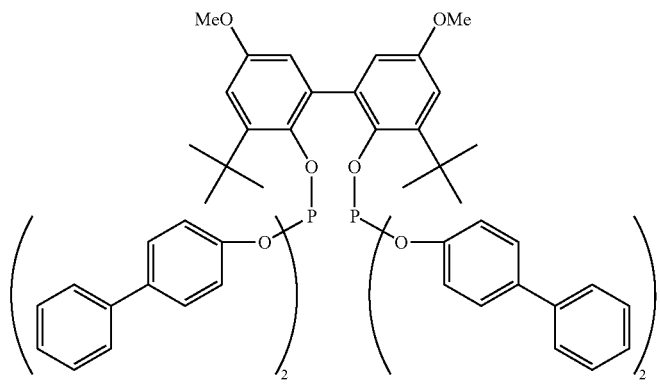
119
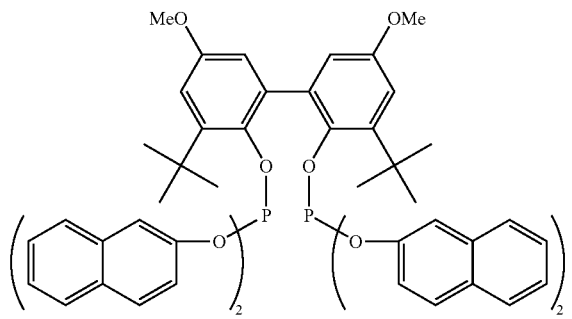
120
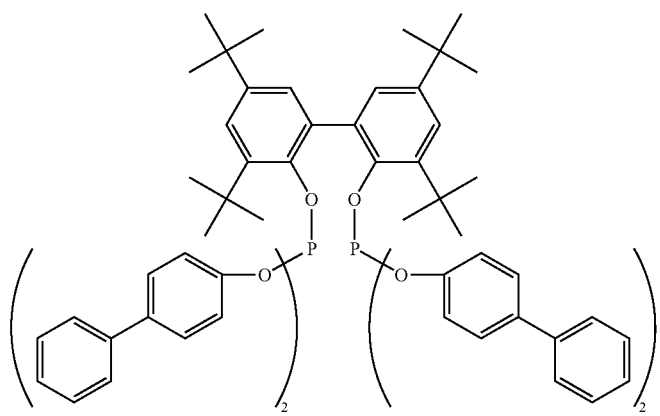
121
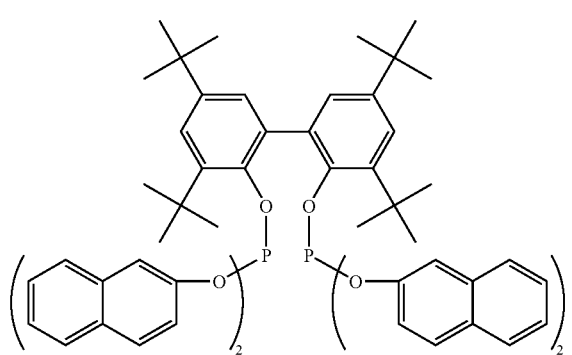
122

-continued
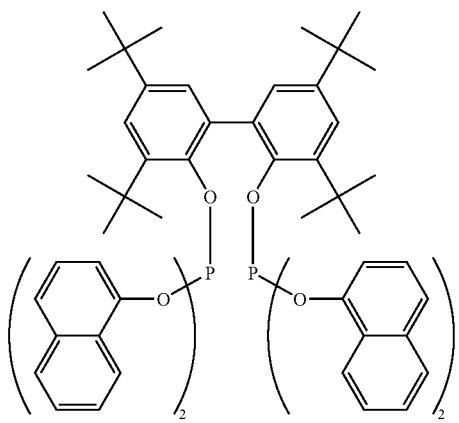
123
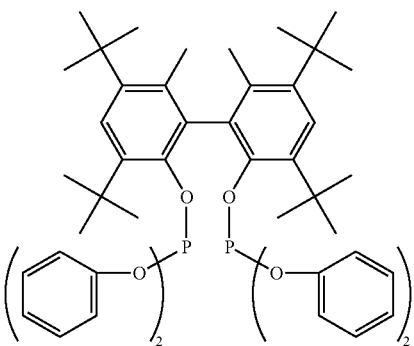
124
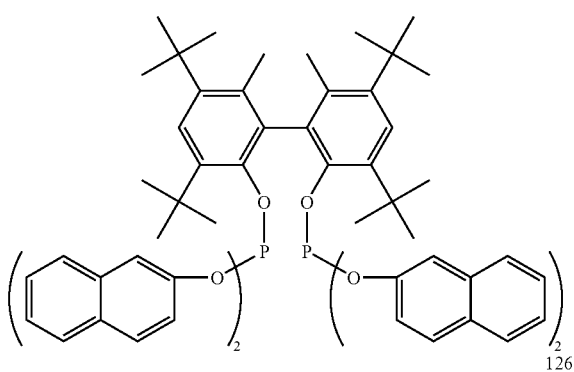
125
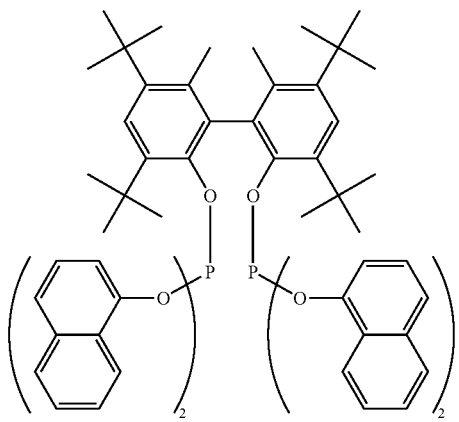
126
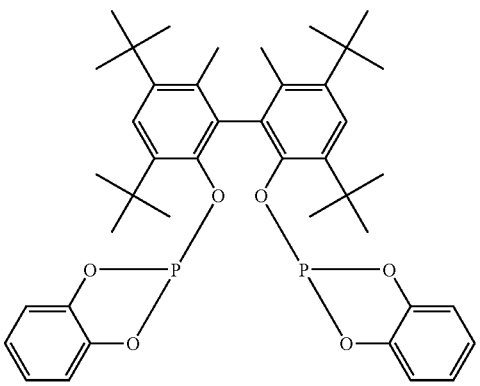
127
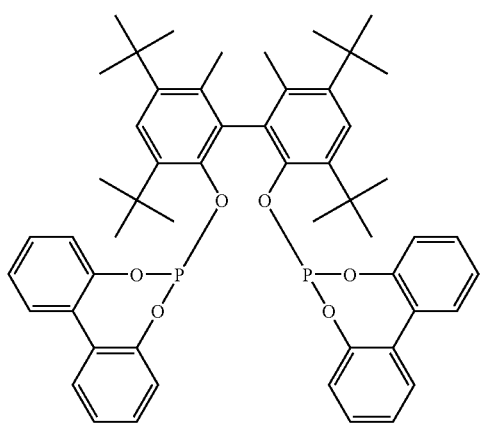
128

Such bisphosphite chelating ligands and other bisphosphite chelating ligands are subject matter of EP-A 213 369 and U.S. Pat. No. 4,769,498 and their preparation is described there.

In place of the abovementioned bisphosphite chelating ligands, it is also possible to use monodentate monophosphite ligands of the formula V $$P(OR^S)(OR^T)(OR^U) \qquad V$$

for complexing the rhodium hydroformylation catalyst and as free ligand in the process of the present invention. The suitability of such ligands and their complexes with rhodium as catalysts for isomerizing hydroformylation is known. In the monophosphite ligands of the formula IV, the radicals $R^S$, $R^T$ and $R^U$ are, independently of one another, identical or different organic groups generally having from 1 to 30, preferably from 5 to 30, carbon atoms, for example substituted or unsubstituted alkyl, aryl, arylalkyl, cycloalkyl and/or heteroaryl groups. Owing to their increased hydrolysis and degradation stability, particular preference is given to sterically hindered monophosphite ligands as are described, for example, in EP-A 155 508. Merely for the purposes of illustration, the following monophosphite ligand structures may be mentioned by way of example:

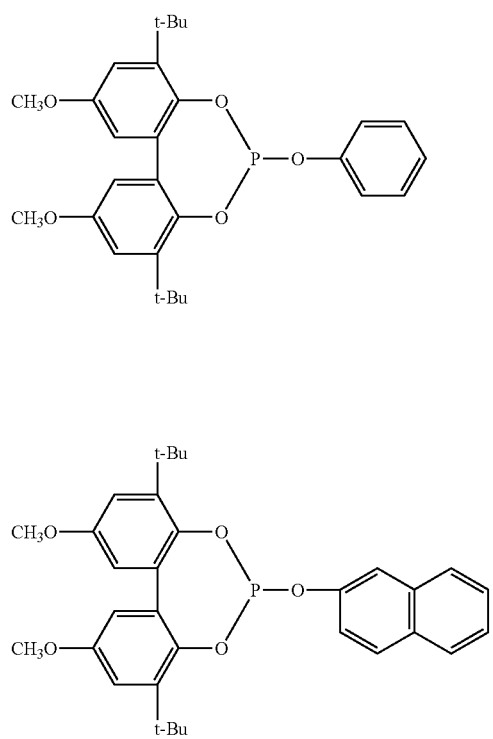

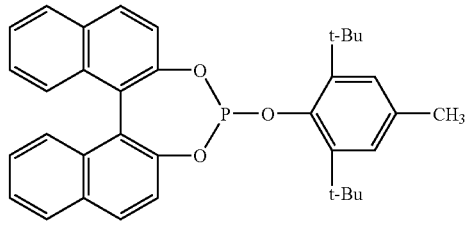

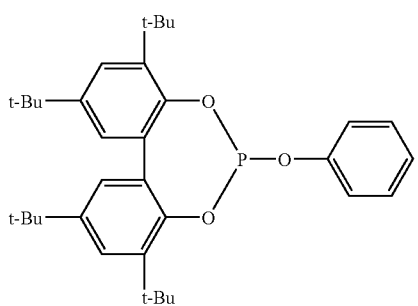

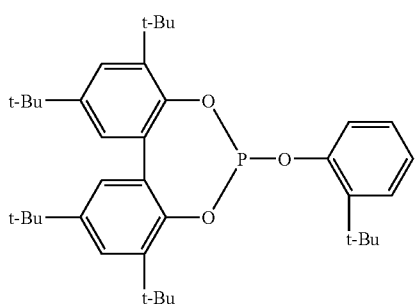

Known ligands for the isomerizing hydroformylation using rhodium complexes as catalysts also include bidentate ligands which have a phosphinite or phosphine group in addition to the phosphite group in the ligand molecule. Such ligands are described, inter alia, in WO 99/50214. Merely for the purposes of illustration, some examples of such ligands are shown below:

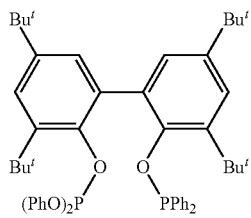

-continued
136
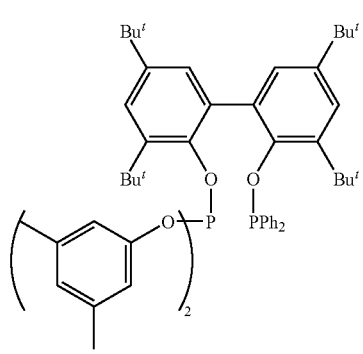
137
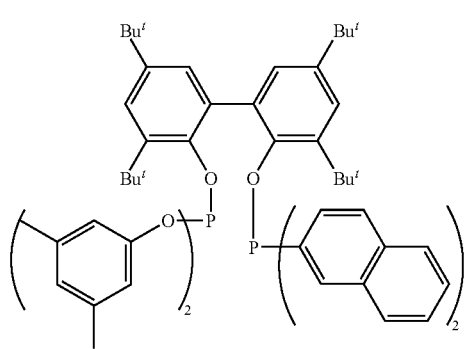
138
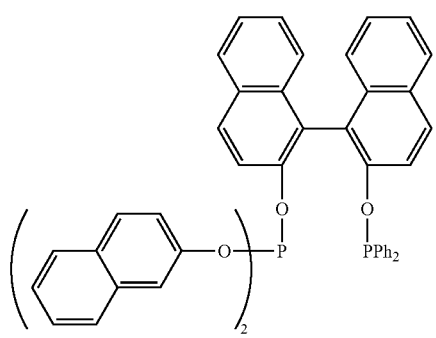
139
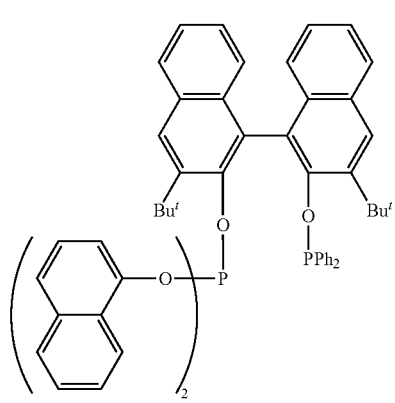
-continued
140
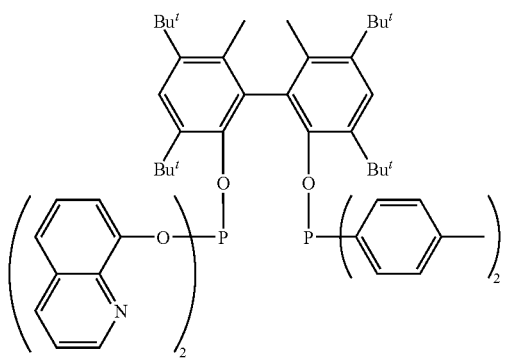
141
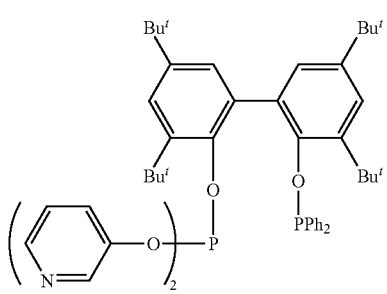
142
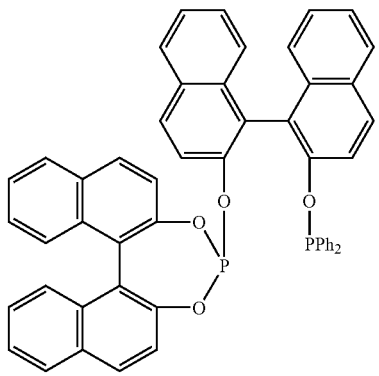
143
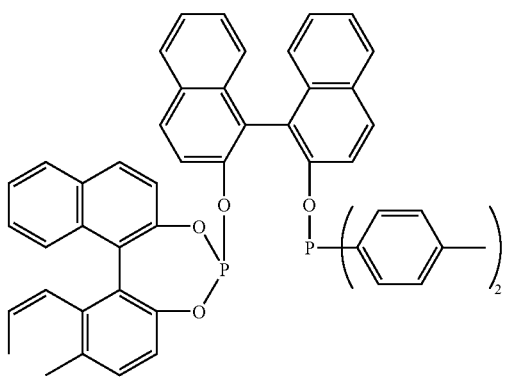

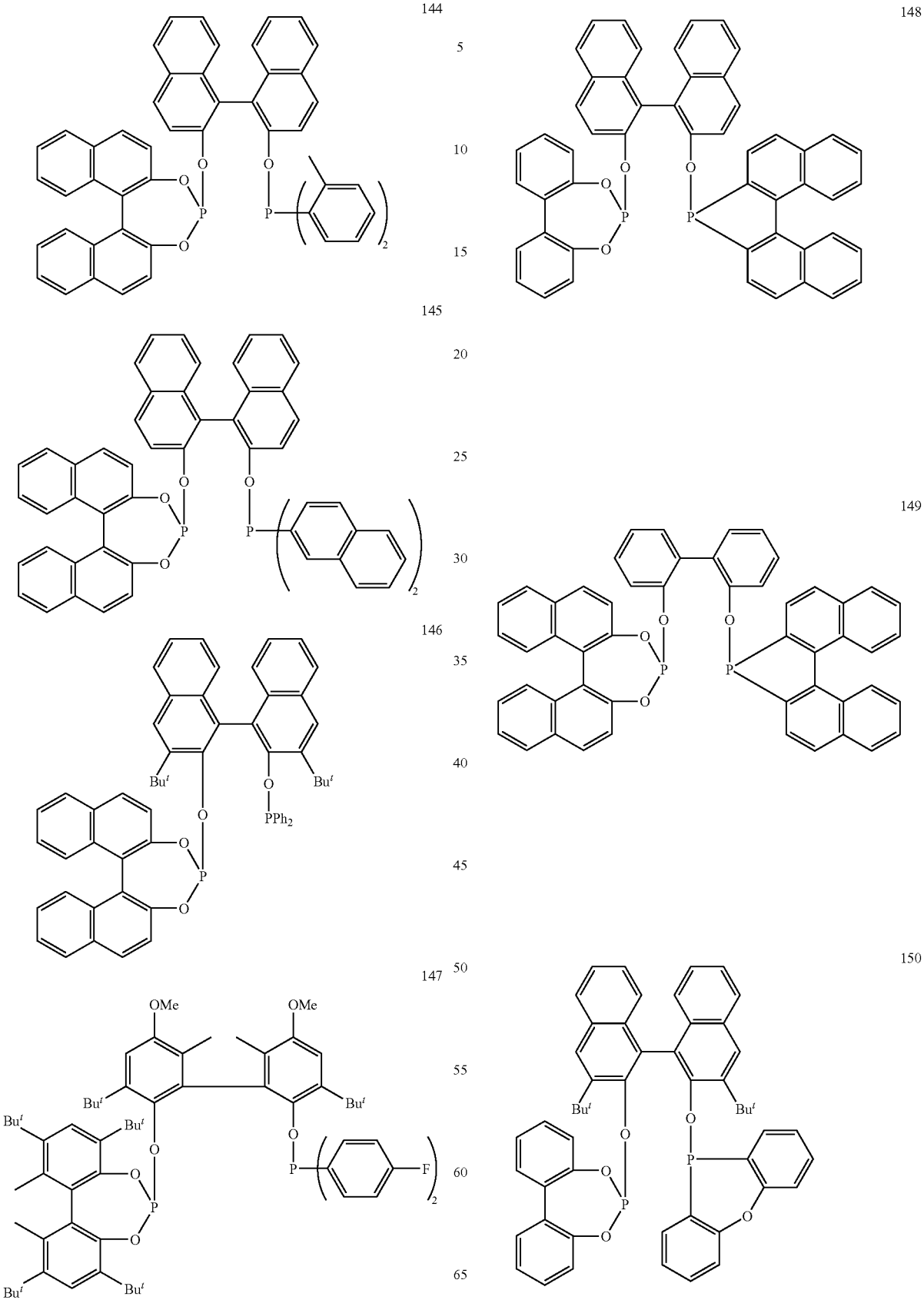

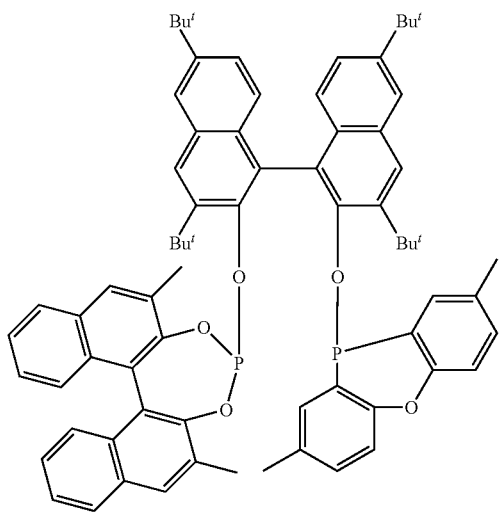

151

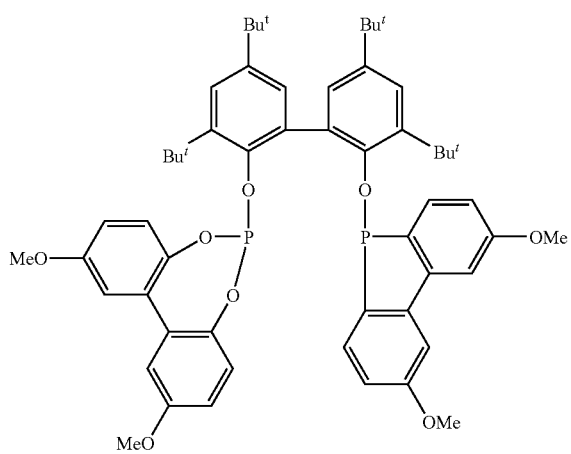

152

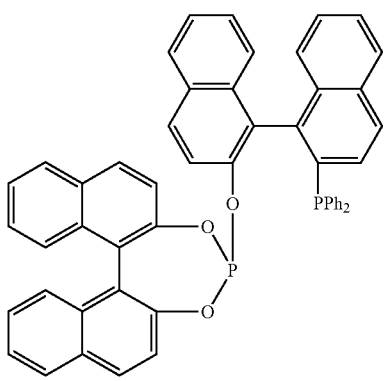

153

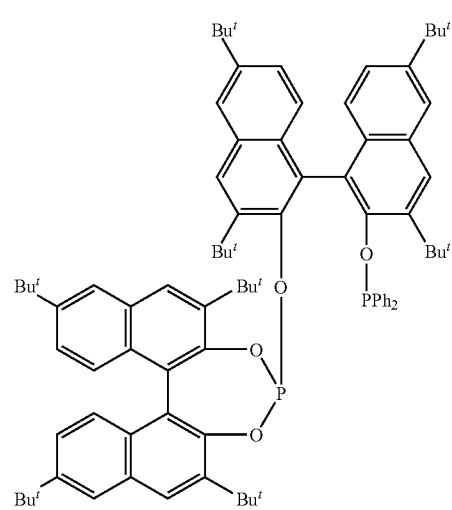

154

Bu$^t$: tertiary butyl
Ph: phenyl

The ligand types described above can be used in the form of their complexes with rhodium and/or as free ligands in the process of the present invention. Preference is given to using rhodium complexes with phosphoramidite ligands having a xanthene backbone, as are described in WO 02/083695, as catalysts for the isomerizing hydroformylation in the process of the present invention.

The process of the present invention makes it possible to hydroformylate olefin compositions comprising both α-olefins and olefins having internal double bonds to give the corresponding aldehydes in an n/i ratio higher than that corresponding to the proportion of α-olefins in the olefin composition and at a higher space-time yield than is obtainable in conventional processes without the cascading into two or more reaction zones according to the present invention.

The process of the present invention is illustrated below with the aid of examples.

EXAMPLES

Synthesis of Ligand 53:

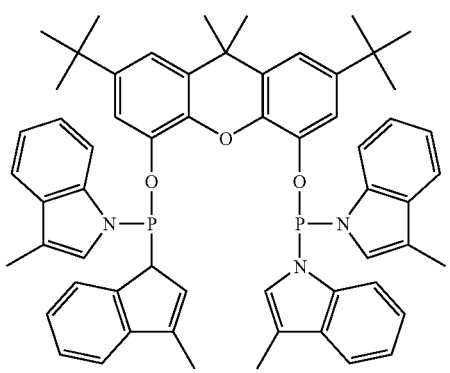

53

28.5 g (218 mmol) of 3-methylindole (skatole) together with about 50 ml of dried toluene were placed in a reaction vessel and the solvent was distilled off under reduced pressure to remove traces of water by azeotropic distillation. This procedure was repeated once more. The residue was subsequently taken up in 700 ml of dried toluene under argon and the mixture was cooled to −65° C. 14.9 g (109 mmol) of $PCl_3$ followed by 40 g (396 mmol) of triethylamine were then added slowly at −65° C. The reaction mixture was brought to room temperature over a period of 16 hours and then refluxed for 16 hours. 19.3 g (58 mmol) of 4,5-dihydroxy-2,7-di-tert-butyl-9,9-dimethylxanthene in 300 ml of dried toluene were added to the reaction mixture, and the mixture was then refluxed for 16 hours and, after cooling to room temperature, the precipitated colorless solid (triethylamine hydrochloride) was filtered off with suction, the solvent was distilled off and the residue was recrystallized twice from hot ethanol. Drying under reduced pressure gave 36.3 g (71% of theory) of a colorless solid. $^{31}$P-NMR (298K): δ =105.

Example 1

Hydroformylation of 1-butene, $CO:H_2$ Molar Ratio=1:1

5.5 mg of $Rh(CO)_2$acac (acac=acetylacetonate) and 200 mg of ligand 53 were weighed out separately, each dissolved in 5 g of toluene, mixed and treated with 10 bar of synthesis gas ($CO:H_2$=1:1) at 90° C. (preactivation). After 1 hour, the mixture was depressurized. 9.9 g of 1-butene were then added via a pressure lock, a total pressure of 17 bar was set by means of synthesis gas ($CO:H_2$=1:1) and hydroformylation was carried out at 90° C. for 2 hours (109 ppm of Rh; ligand 53:Rh molar ratio≈10:1). After the reaction time indicated, the autoclave was cooled, carefully vented via a cold trap and the collected reaction product mixtures (reactor and cold trap) were analyzed by means of gas chromatography. The conversion was 99%, the yield of valeraldehyde was 92% and the linearity (proportion of n product) was 98.5%. The yield of 2-butene (isomerization product) was 7%.

The CO and $H_2$ partial pressures at the beginning of the reaction were each 6 bar.

The linearity (proportion of n product) is defined as the amount of n-valeraldehyde divided by the sum of n-valeraldehyde and i-valeraldehyde multiplied by 100.

Example 2

Hydroformylation of 1-butene, $CO:H_2$ Molar Ratio=1:2

5.4 mg of $Rh(CO)_2$acac (acac=acetylacetonate) and 200 mg of ligand 53 were weighed out separately, each dissolved in 5 g of toluene, mixed and treated with 10 bar of synthesis gas ($CO:H_2$=1:2) at 90° C. (preactivation). After 1 hour, the mixture was depressurized. 10.1 g of 1-butene were then added via a pressure lock, and a total pressure of 17 bar was set by means of synthesis gas ($CO:H_2$=1:2). The gas feed was then changed over to synthesis gas ($CO:H_2$=1:1) to ensure a constant $CO:H_2$ molar ratio of 1:2 in the reactor. Hydroformylation was subsequently carried out at 90° C. for 2 hours (105 ppm of Rh; ligand 53:Rh molar ratio≈10:1). The conversion was 98%, the yield of valeraldehyde was 49% and the linearity (proportion of n product) was 95.8%. The yield of 2-butene (isomerization product) was 46%.

The CO partial pressure at the beginning of the reaction was 4 bar, and the $H_2$ partial pressure at the beginning of the reaction was 8 bar.

Example 3

Hydroformylation of 2-butene, $CO:H_2$ Molar Ratio=1:1

5.0 mg of $Rh(CO)_2$acac (acac=acetylacetonate) and 176 mg of ligand 53 were weighed out separately, each dissolved in 5 g of toluene, mixed and treated with 10 bar of synthesis gas ($CO:H_2$=1:1) at 90° C. (preactivation). After 1 hour, the mixture was depressurized. 11.3 g of 2-butene were then added via a pressure lock, and a total pressure of 17 bar was set by means of synthesis gas ($CO:H_2$=1:1). Hydroformylation was subsequently carried out at 90° C. for 4 hours (93 ppm of Rh; ligand 53:Rh molar ratio≈10:1). The conversion was 12%, the yield of valeraldehyde was 10% and the linearity (proportion of n product) was 88.5%.

The CO and $H_2$ partial pressures at the beginning of the reaction were each 6 bar.

Example 4

Hydroformylation of 2-butene, $CO:H_2$ Molar Ratio=1:2

5.0 mg of $Rh(CO)_2$acac (acac=acetylacetonate) and 176 mg of ligand 53 were weighed out separately, each dissolved in 5 g of toluene, mixed and treated with 10 bar of synthesis gas ($CO:H_2$=1:2) at 90° C. (preactivation). After 1 hour, the mixture was depressurized. 11.2 g of 2-butene were then added via a pressure lock, and a total pressure of 17 bar was set by means of synthesis gas ($CO:H_2$=1:2). The gas feed was then changed over to synthesis gas ($CO:H_2$=1:1) to ensure a constant $CO:H_2$ molar ratio of 1:2 in the reactor. Hydroformylation was subsequently carried out at 90° C. for 4 hours (93 ppm of Rh; ligand 53:Rh molar ratio≈10:1). The conversion was 34%, the yield of valeraldehyde was 32% and the linearity (proportion of n product) was 93%.

The CO partial pressure at the beginning of the reaction was 4 bar, and the $H_2$ partial pressure at the beginning of the reaction was 8 bar.

Example 5

Hydroformylation of 2-butene, $CO:H_2$ Molar Ratio=1:9

5.0 mg of $Rh(CO)_2$acac (acac=acetylacetonate) and 176 mg of ligand 53 were weighed out separately, each dissolved in 5 g of toluene, mixed and treated with 10 bar of synthesis gas ($CO:H_2$=1:9) at 90° C. (preactivation). After 1 hour, the mixture was depressurized. 11.2 g of 2-butene were then added via a pressure lock, and a total pressure of 17 bar was set by means of synthesis gas ($CO:H_2$=1:9). The gas feed was then changed over to synthesis gas ($CO:H_2$=1:1) to ensure a constant $CO:H_2$ molar ratio of 1:9 in the reactor. Hydroformylation was subsequently carried out at 90° C. for 4 hours (93 ppm of Rh; ligand 53:Rh molar ratio≈10:1). The conversion was 64%, the yield of valeraldehyde was 46% and the linearity (proportion of n product) was 96%.

The CO partial pressure at the beginning of the reaction was 1.2 bar, and the $H_2$ partial pressure at the beginning of the reaction was 10.8 bar.

Example 6

Hydroformylation of trans-2-butene, CO:H$_2$=1:1

5.0 mg of Rh(CO)$_2$acac (acac=acetylacetonate) and 187 mg of ligand 53 were weighed out separately, each dissolved in 5 g of toluene, mixed and treated with 10 bar of synthesis gas (CO:H$_2$=1:1) at 90° C. (preactivation). After 1 hour, the mixture was depressurized. 10.4 g of trans-2-butene were then added via a pressure lock and a total pressure of 12 bar was set by means of synthesis gas (CO:H$_2$=1:1).

Hydroformylation was subsequently carried out at 90° C. for 4 hours (97 ppm of Rh; ligand 53:Rh=10:1). The conversion was 33%, the yield of valeraldehyde was 30% and the linearity (proportion of n product) was 95%.

The CO and H$_2$ partial pressures at the beginning of the reaction were each 3.5 bar.

Example 7

Continuous Hydroformylation of Raffinate II Using Rh/Ligand 53

In a continuously operated apparatus as shown in the drawing, comprising two stirring autoclaves (1 and 2) which each had a liquid capacity of 1 l and were connected in series, a pressure separator (3), a depressurized and heated container for separating off C4-hydrocarbons (4) and a wiped film evaporator (5) for separating the catalyst-containing high boiler phase from the product phase, raffinate II (29% by weight of 1-butene, 52% by weight of 2-butene, 19% by weight of butanes and other C4-hydrocarbons) was hydroformylated using rhodium and ligand 53 as catalyst. The catalyst return stream from the distillation (5) to the reactors was about 130 g/h, and the raffinate feed rate was about 70 g/h. The rhodium concentration in the reactors was about 100 ppm at a ligand/metal molar ratio of ≈10:1 (mol:mol), and the temperature of the first reactor was 70° C. and that of the second reactor was 90° C. The first reactor was supplied with synthesis gas having a CO:H$_2$ molar ratio of 1:1 and was operated at a total pressure of about 22 bar. Additional introduction of H$_2$ into the second reactor, which was operated at about 20 bar, enabled the CO content of the synthesis gas to be regulated via the offgas concentration to any value in the range from about 50% of CO to about 1% of CO. In steady-state operation at a CO:H$_2$ molar ratio of 1:25 in the second reactor (first reactor: CO:H$_2$ molar ratio=1:1) over a representative period of 13 days, an aldehyde yield of 49% and a proportion of n product of 96.1% were achieved.

We claim:

1. A process for the continuous preparation of an aldehyde having from 5 to 21 carbon atoms by isomerizing hydroformylation in the homogeneous phase of an olefin composition having from 4 to 20 carbon atoms and comprising an α-olefin or an olefin having internal double bonds by means of a synthesis gas in the presence of a homogeneous rhodium catalyst complexed with an oxygen- and/or nitrogen-containing organophosphorus ligand and free ligand at elevated temperature and elevated pressure in a multistage reaction system comprising at least two reaction zones, wherein the olefin composition is firstly reacted with the synthesis gas having a CO/H$_2$ molar ratio of from 4:1 to 1:2 at a total pressure of from 10 to 40 bar in a group of one or more first reaction zones to a conversion of the α-olefin of from 40 to 95% and the hydroformylation mixture from this group of one or more first reaction zones is reacted with the synthesis gas having a CO/H$_2$ molar ratio of from 1:4 to 1:1000 at a total pressure of from 5 to 30 bar in a group of one or more downstream reaction zones, where the total pressure in the one or more downstream reaction zones is in each case from 1 to (T1−Tf) bar lower than in the preceding reaction zone, where T1 is the total pressure in the preceding reaction zone and Tf is the total pressure in the reaction zone downstream of the one or more first reaction zones, with the proviso that the difference T1−Tf is greater than 1 bar, and the CO partial pressure in the one or more downstream reaction zones is in each case lower than in the reaction zone preceding this reaction zone wherein the catalyst used is a complex of rhodium with a phosphoramidite ligand of the formula I

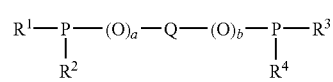

where
Q is a bridging group of the formula

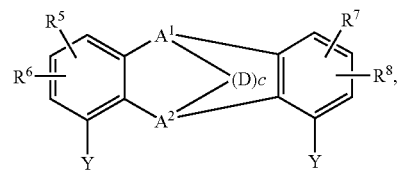

where
A$^1$ and A$^2$ are each, independently of one another, O, S, SiR$^a$R$^b$, NR$^c$ or CR$^d$R$^e$, where
R$^a$, R$^b$ and R$^c$ are each, independently of one another, hydrogen, alkyl, cycloalkyl, heterocycloalkyl, aryl or hetaryl,
R$^d$ and R$^e$ are each, independently of one another, hydrogen, alkyl, cycloalkyl, heterocycloalkyl, aryl or hetaryl or together with the carbon atom to which they are bound form a cycloalkylidene group having from 4 to 12 carbon atoms or the group R$^d$ together with a further group R$^d$ or the group R$^e$ together with a further group R$^e$ forms an intramolecular bridging group D,
D is a divalent bridging group selected from group consisting of

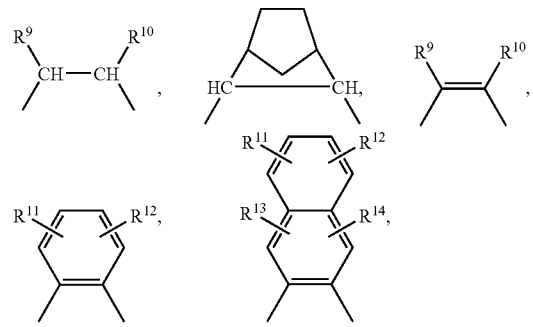

where
R$^9$ and R$^{10}$ are each, independently of one another, hydrogen, alkyl, cycloalkyl, aryl, halogen, trifluoromethyl, carboxyl, carboxylate or cyano or are joined to one another to form a C$_3$- to C$_4$-alkylene bridge,
R$^{11}$, R$^{12}$, R$^{13}$ and R$^{14}$ are each, independently of one another, hydrogen, alkyl, cycloalkyl, aryl, halogen, trifluoromethyl, COOH, carboxylate, cyano, alkoxy, SO$_3$H, sulfonate, NE$^1$E$^2$, alkylene-NE$^1$E$^2$E$^{3+}$X$^-$, acyl or nitro, c is 0 or 1, Y is a chemical bond, R$^5$, R$^6$, R$^7$ and R$^8$ are each, independently of one another, hydrogen, alkyl, cycloalkyl, heterocycloalkyl, aryl, hetaryl, COOR$^f$, COO$^-$M$^+$, SO$_3$R$^f$, SO$^-_3$M$^+$, NE$^1$E$^2$, NE$^1$E$^2$E$^{3+}$X$^-$, alkylene-NE$^1$E$^2$E$^{3+}$X$^-$, OR$^f$, SR$^f$, (CHR$^g$CH$_2$O)$_x$R$^f$, (CH$_2$N(E$^1$))$_x$R$^f$, (CH$_2$CH$_2$N(E$^1$))$_x$R$^f$, halogen, trifluoromethyl, nitro, acyl or cyano, where R$^f$, E$^1$, E$^2$ and E$^3$ are identical or different radicals selected from among hydrogen, alkyl, cycloalkyl and aryl, R$^g$ is hydrogen, methyl or ethyl, M$^+$ is a cation, X$^-$ is an anion and x is an integer from 1 to 120, or R$^5$ and/or R$^7$ together with two adjacent carbon atoms of the benzene ring to which they are bound form a fused ring system having 1, 2 or 3 further rings, a and b are each, independently of one another, 0 or 1, P is a phosphorus atom, and R$^1$, R$^2$, R$^3$, R$^4$ are each, independently of one another, hetaryl, hetaryloxy, alkyl, alkoxy, aryl, aryloxy, cycloalkyl, cycloalkoxy, heterocycloalkyl, heterocycloalkoxy or an NE$^1$E$^2$ group, with the proviso that R$^1$ and R$^3$ are bound via the nitrogen atom of pyrrole groups bound to the phosphorus atom P or R$^1$ together with R$^2$ and/or R$^3$ together with R$^4$ form a divalent group E which contains at least one pyrrole group bound via the pyrrole nitrogen to the phosphorus atom P and has the formula Py-I-W where Py is a pyrrole group, I is a chemical bond or O, S, SiR$^a$R$^b$, NR$^c$ or CR$^h$R$^i$, W is cycloalkyl, cycloalkoxy, aryl, aryloxy, hetaryl or hetaryloxy, and R$^h$ and R$^i$ are each, independently of one another, hydrogen, alkyl, cycloalkyl, heterocycloalkyl, aryl or hetaryl, or form a bispyrrole group which is bound via the nitrogen atoms to the phosphorus atom P and has the formula Py-I-Py.

2. A process as claimed in claim 1, wherein a CO/H$_2$ molar ratio of from 3:2 to 2:3 is set in said one or more first reaction zones and a CO/H$_2$ molar ratio of from 1:9 to 1:100 is set in said one or more downstream reaction zones.

3. A process as claimed in claim 1, which is carried out in two reaction zones.

4. A process as claimed in claim 2, wherein the CO/H$_2$ molar ratio in said one or more reaction zones downstream of said one or more of first reaction zones is set by hydrogen-containing offgases from the aldehyde and enal hydrogenation processes.

5. A process for the continuous preparation of an aldehyde having from 5 to 21 carbon atoms by isomerizing hydroformylation in the homogeneous phase of an olefin composition having from 4 to 20 carbon atoms and comprising an α-olefin or an olefin having internal double bonds by means of a synthesis gas in the presence of a homogeneous rhodium catalyst complexed with an oxygen- and/or nitrogen-containing organophosphorus ligand and free ligand at elevated temperature and elevated pressure in a multistage reaction system comprising at least two reaction zones, wherein the olefin composition is firstly reacted with the synthesis gas having a CO/H$_2$ molar ratio of from 4:1 to 1:2 at a total pressure of from 10 to 40 bar in a group of one or more first reaction zones to a conversion of the α-olefin of from 40 to 95% and the hydroformylation mixture from this group of one or more first reaction zones is reacted with the synthesis gas having a CO/H$_2$ molar ratio of from 1:4 to 1:1000 at a total pressure of from 5 to 30 bar in a group of one or more downstream reaction zones, where the total pressure in the one or more downstream reaction zones is in each case from 1 to (T1 −Tf) bar lower than in the preceding reaction zone, where T1 is the total pressure in the preceding reaction zone and Tf is the total pressure in the reaction zone downstream of the one or more first reaction zones, with the proviso that the difference T1 −Tf is greater than I bar, and the CO partial pressure in the one or more downstream reaction zones is in each case lower than in the reaction zone preceding this reaction zone wherein the catalyst used is a complex of rhodium with a phosphoramidite ligand of the formula Ia

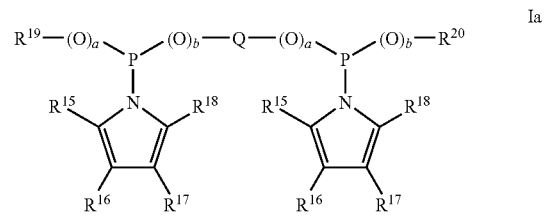

where

R$^{15}$, R$^{16}$, R$^{17}$ and R$^{18}$ are each, independently of one another, hydrogen, alkyl, cycloalkyl, heterocycloalkyl, aryl, hetaryl, W'COOR$^k$, W'COO$^-$M$^+$, W'(SO$_3$)R$^k$, W'(SO$_3$)$^-$M$^+$, W'PO$_3$(R$^k$)(R$^l$), W'(PO$_3$)$_2^-$(M$^+$)$_2$, W'NE$^4$E$^5$, W'(NE$^4$E$^5$E$^6$)$^+$X$^-$, W'OR$^k$, W'SR$^k$, (CHR$^1$CH$_2$O)$_y$R$^k$, (CH$_2$NE$^4$)$_y$R$^k$, (CH$_2$CH$_2$NE$^4$)$_y$R$^k$, halogen, trifluoromethyl, nitro, acyl or cyano, where W' is a single bond, a heteroatom or a divalent bridging group having from 1 to 20 bridge atoms, R$^k$, E$^4$, E$^5$, E$^6$ are identical or different radicals selected from among hydrogen, alkyl, cycloalkyl and aryl, R$^1$ is hydrogen, methyl or ethyl, M$^+$ is a cation equivalent, X$^-$ is an anion equivalent and y is an integer from 1 to 240, where two adjacent radicals R$^{15}$, R$^{16}$, R$^{17}$ and R$^{18}$ together with the carbon atoms of the pyrrole ring to which they are bound may also form a fused ring system having 1, 2 or 3 further rings, with the proviso that at least one of the radicals R$^{15}$, R$^{16}$, R$^{17}$ and R$^{18}$ is not hydrogen and R$^{19}$ and R$^{20}$ are not linked to one another, R$^{19}$ and R$^{20}$ are each, independently of one another, cycloalkyl, heterocycloalkyl, aryl or hetaryl, a and b are each, independently of one another, 0 or 1,
P is a phosphorus atom,
Q is a bridging group of the formula

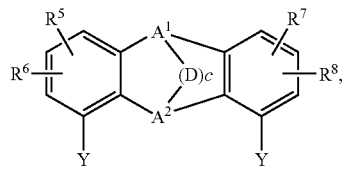

where
A$^1$ and A$^2$ are each, independently of one another, O, S, SiR$^a$R$^b$, NR$^c$ or CR$^d$R$^e$, where
R$^a$, R$^b$ and R$^c$ are each, independently of one another, hydrogen, alkyl, cycloalkyl, heterocycloalkyl, aryl or hetaryl,
R$^d$ and R$^e$ are each, independently of one another, hydrogen, alkyl, cycloalkyl, heterocycloalkyl, aryl or hetaryl or together with the carbon atom to which they are bound form a cycloalkylidene group having from 4 to 12 carbon atoms or the group R$^d$ together with a further group R$^d$ or the group R$^e$ together with a further group R$^e$ forms an intramolecular bridging group D,
D is a divalent bridging group selected from among the groups

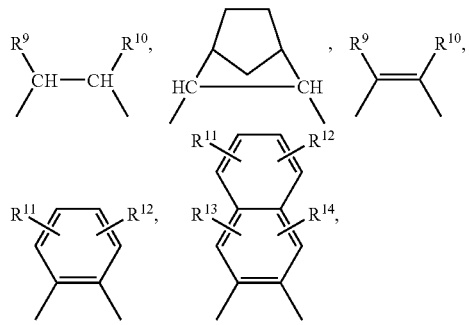

where
R$^9$ and R$^{10}$ are each, independently of one another, hydrogen, alkyl, cycloalkyl, aryl, halogen, trifluoromethyl, carboxyl, carboxylate or cyano or are joined to one another to form a C$_3$- to C$_4$-alkylene bridge, R$^{11}$, R$^{12}$, R$^{13}$ and R$^{14}$ are each, independently of one another, hydrogen, alkyl, cycloalkyl, aryl, halogen, trifluoromethyl, COOH, carboxylate, cyano, alkoxy, SO$_3$H, sulfonate, NE$^1$E$^2$, alkylene-NE$^1$E$^2$E$^{3+}$X$^-$, acyl or nitro,
c is 0 or 1,
R$^5$, R$^6$, R$^7$ and R$^8$ are each, independently of one another, hydrogen, alkyl, cycloalkyl, heterocycloalkyl, aryl, hetaryl, COOR$^f$, COO$^-$M$^+$, SO$_3$R$^f$, SO$^-$$_3$M$^+$, NE$^1$E$^2$, NE$^1$E$^2$E$^{3+}$X$^-$, alkylene-NE$^1$E$^2$E$^{3+}$X$^-$, OR$^f$, SR$^f$, (CHR$^g$CH$_2$O)$_x$R$^f$, (CH$_2$N(E$^1$))$_x$R$^f$, (CH$_2$CH$_2$N(E$^1$))$_x$R$^f$, halogen, trifluoromethyl, nitro, acyl or cyano,
where
R$^f$, E$^1$, E$^2$ and E$^3$ are identical or different radicals selected from among hydrogen, alkyl, cycloalkyl and aryl,
R$^g$ is hydrogen, methyl or ethyl,
M$^+$ is a cation,
X$^-$ is an anion and
x is an integer from 1 to 120,
or
R$^5$ and/or R$^7$ together with two adjacent carbon atoms of the benzene ring to which they are bound form a fused ring system having 1, 2 or 3 further rings.

6. A process as claimed in claim 1, wherein the olefin composition used is a raffinate II.

7. A process as claimed in claim 5, wherein a CO/H$_2$ molar ratio of from 3:2 to 2:3 is set in said one or more first reaction zones and a CO/H$_2$ molar ratio of from 1:9 to 1:100 is set in said one or more downstream reaction zones.

8. A process as claimed in claim 5, which is carried out in two reaction zones.

9. A process as claimed in claim 7, which is carried out in two reaction zones.

10. A process as claimed in claim 7, wherein the CO/H$_2$ molar ratio in said one or more reaction zones downstream of said one or more of first reaction zones is set by hydrogen-containing offgases from the aldehyde and enal hydrogenation processes.

11. A process as claimed in claim 9, wherein the CO/H$_2$ molar ratio in said one or more reaction zones downstream of said one or more of first reaction zones is set by hydrogen-containing offgases from the aldehyde and enal hydrogenation processes.

12. A process as claimed in claim 4, which is carried out in two reaction zones.

* * * * *